(12) United States Patent
Magar et al.

(10) Patent No.: US 7,754,722 B2
(45) Date of Patent: Jul. 13, 2010

(54) PIPERAZINE DERIVATIVES AND METHODS OF USE

(75) Inventors: Sharad Magar, Canton, MA (US); Andreas Goutopoulos, Boston, MA (US); Yihua Liao, Westwood, MA (US); Matthias Schwarz, Thonex (CH); Russell J. Thomas, Siena (IT)

(73) Assignee: Merck Serono SA, Coinsins, Vaud (CH)

( * ) Notice: Subject to any disclaimer, the term of this patent is extended or adjusted under 35 U.S.C. 154(b) by 1032 days.

(21) Appl. No.: 10/528,437

(22) PCT Filed: Sep. 19, 2003

(86) PCT No.: PCT/EP03/50640

§ 371 (c)(1), (2), (4) Date: Apr. 10, 2006

(87) PCT Pub. No.: WO2004/031182

PCT Pub. Date: Apr. 15, 2004

(65) Prior Publication Data

US 2006/0223813 A1    Oct. 5, 2006

Related U.S. Application Data

(60) Provisional application No. 60/412,308, filed on Sep. 20, 2002.

(51) Int. Cl.
*A61K 31/497*    (2006.01)
*C07D 241/04*    (2006.01)
*C07D 295/00*    (2006.01)
*C07D 403/00*    (2006.01)

(52) U.S. Cl. .................. 514/252.13; 544/358; 544/359; 544/390; 544/392

(58) Field of Classification Search ............ 514/252.13; 544/358, 386, 359, 390, 392
See application file for complete search history.

(56) References Cited

U.S. PATENT DOCUMENTS

| 5,017,557 | A  | 5/1991 | Fabbri et al. |
| 5,639,639 | A  | 6/1997 | Reddy et al. |
| 5,767,067 | A  | 6/1998 | Arpaia et al. |
| 5,880,128 | A  | 3/1999 | Doll et al. |
| 6,235,755 | B1 | 5/2001 | El Tayer et al. |
| 6,423,723 | B1 | 7/2002 | Tayer et al. |
| 6,432,959 | B1 | 8/2002 | Cooper et al. |

FOREIGN PATENT DOCUMENTS

| JP | 2001-294572 | 10/2001 |
| WO | WO 96/31478 | 10/1996 |
| WO | WO 98/57960 | 12/1998 |
| WO | WO 99/26921 | 6/1999 |
| WO | WO 00/08015 | 2/2000 |
| WO | WO 00/39119 | 7/2000 |
| WO | WO 02/09706 | 2/2002 |

OTHER PUBLICATIONS

Patani et. al., Chemical Rev., 1996, American Chemical Society, 96, 3147-3176.*
Breitenbucher, J., et al., "Generation of a Piperazine-2-Carobxamide Library: A Practical Application of the Phenol-Sulfide React and Release Linker," Tetrahedron Letters 39, No. 11, pp. 1295-1298 (1998).
Kelton, C., et al., "The Cloning of the Human Follicle Stimulating Hormone Receptor and Its Expression in COS-7, CHO, and Y-1 Cells," Molecular and Cellular Endocrinology, vol. 89, pp. 141-151 (1992).
The Merck Manual, Sixteenth Edition, vol. 2, pp. 12-17, (1992).

* cited by examiner

*Primary Examiner*—Sreeni Padmanabhan
*Assistant Examiner*—Sarah Pihonak
(74) *Attorney, Agent, or Firm*—Howrey LLP

(57) ABSTRACT

The invention provides 2-carboxamide piperazine compounds of formula I, $R^3.IN\backslash'N\sim'R^2I(0)z\text{-}oR^4I$ wherein R', $R^2$, $R^3$ and $R^4$ are as defined in the claims and methods of treatment and pharmaceutical compositions that utilize or comprise one or more such compounds. Compounds of the invention are useful for the treatment of mammalian infertility.

27 Claims, No Drawings

PIPERAZINE DERIVATIVES AND METHODS OF USE

CROSS REFERENCE TO RELATED APPLICATIONS

This application is a national stage application of International Application No. PCT/EP2003/050640, filed Sep. 19, 2003, which claims priority to U.S. Provisional Application No. 60/412,308, filed Sep. 20, 2002, each of which is incorporated in its entirety by reference herein.

BACKGROUND OF THE INVENTION

1. Field of the Invention

The present invention relates to 2-carboxamide piperazine compounds, and methods of treatment and pharmaceutical compositions that utilize or comprise one or more such compounds. Compounds of the invention are useful for the treatment of mammalian infertility.

2. Background

Luteinizing Hormone (LH) and Follicle Stimulating Hormone (FSH) are produced by the anterior pituitary gland and are involved in mammalian reproductive processes. The glycoprotein family of pituitary hormones such as FSH, LH and the thyrotropic hormone (TSH) relatively large heterodimeric proteins that contain carbohydrate moieties. They have a common α-subunit and distinct β-subunits (1-4) providing receptor recognition and specificity.

LH is released from the anterior pituitary gland under the influence of gonadotropin releasing hormone and progesterins. In the female LH stimulates ovulation and is the major hormone involved in the regulation of progesterone secretion by the corpus luteum. In the male, LH stimulates Leydig cells to secrete androgens, particularly testosterone.

FSH is released from the anterior pituary under the influence of the gonadotrophin releasing hormone, and oestrogens and from the placenta during pregnancy. FSH acts on the ovaries stimulating maturation of follicles and regulates secretion of oestrogens. In the male, FSH is responsible for the integrity of the seminiferous tubules and acts on Sertoli cells to support gametogenesis.

The LH and FSH receptors belong to the superfamily of G-protein coupled receptors, which are complex transmembrane proteins characterized by seven hydrophobic helices. The LH and FSH receptors also share close sequence homology (approximately 40%). The receptors' extracellular domains bind to their respective hormones with high affinity and specificity. The intracellular portions of FSH and LH receptors are coupled to a Gs protein. Receptor activation upon the hormonal interaction with the extracellular domain results in a cascade of events that leads to specific biological effects.

LH and FSH have been used for the treatment of female infertility and spermatogenesis disorders. See U.S. Pat. Nos. 5,767,067; 5,639,639; and 5,017,557.

However, those therapies have some notable shortcomings. For instance, current FSH treatment is limited by lack of oral bioavailability, high costs and need of close medical personnel supervision throughout an administration protocol.

Certain non-peptidic FSH agonists also have been disclosed. See, for instance, U.S. Pat. Nos. 6,235,755; 6,423,723; WO 00/08015; and WO 02/09706.

Thus, it would be desirable to have new agents and methods to treat infertility in mammals.

SUMMARY OF THE INVENTION

We have now found that 2-carboxamide piperazine compounds are potent Follicle Stimulating Hormone receptor (FSH) agonists. Compounds of the invention are particularly useful for treatment of infertility in mammals.

More specifically, in a preferred aspect of the invention, preferred 2-carboxamide piperazine compounds of the invention include those of the following Formula I:

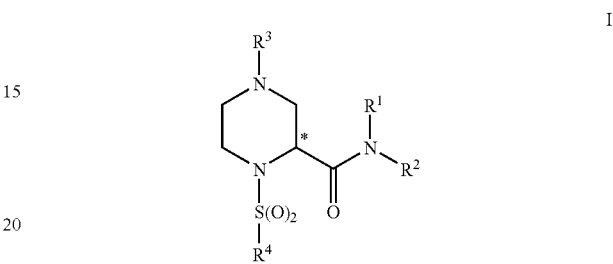

wherein $R^1$ and $R^2$ are independently selected from the group comprising or consisting of hydrogen, $C_1$-$C_{12}$-alkyl, $C_2$-$C_{12}$-alkenyl, $C_2$-$C_{12}$-alkynyl, wherein said alkyl, alkenyl, alkynyl chains may be interrupted by a heteroatom selected from N, O or S, aryl, heteroaryl, saturated or unsaturated 3-8-membered cycloalkyl, heterocycloalkyl, wherein said cycloalkyl, heterocycloalkyl, aryl or heteroaryl groups may be fused with 1-2 further cycloalkyl, heterocycloalkyl, aryl or heteroaryl group, an acyl moiety, $C_1$-$C_{12}$-alkyl aryl, $C_1$-$C_{12}$-alkyl heteroaryl, $C_2$-$C_{12}$-alkenyl aryl, $C_2$-$C_{12}$-alkenyl heteroaryl, $C_2$-$C_{12}$-alkynyl aryl, $C_2$-$C_{12}$-alkynyl heteroaryl, $C_1$-$C_{12}$-alkyl cycloalkyl, $C_1$-$C_{12}$-alkyl heterocycloalkyl, $C_2$-$C_{12}$-alkenyl cycloalkyl, $C_2$-$C_{12}$-alkenyl heterocycloalkyl, $C_2$-$C_{12}$-alkynyl cycloalkyl, $C_2$-$C_{12}$-alkynyl heterocycloalkyl, alkoxycarbonyl, aminocarbonyl, $C_1$-$C_{12}$-alkyl carboxy, $C_1$-$C_{12}$-alkyl acyl, aryl acyl, heteroaryl acyl, $C_3$-$C_8$-(hetero)cycloalkyl acyl, $C_1$-$C_{12}$-alkyl acyloxy, $C_1$-$C_{12}$-alkyl alkoxy, $C_1$-$C_{12}$-alkyl alkoxycarbonyl, $C_1$-$C_{12}$-alkyl aminocarbonyl, $C_1$-$C_{12}$-alkyl acylamino, acylamino, $C_1$-$C_{12}$-alkyl ureido, $C_1$-$C_{12}$-alkyl carbamate, $C_1$-$C_{12}$-alkyl amino, $C_1$-$C_{12}$-alkyl ammonium, $C_1$-$C_{12}$-alkyl sulfonyloxy, $C_1$-$C_{12}$-alkyl sulfonyl, $C_1$-$C_{12}$-alkyl sulfinyl, $C_1$-$C_{12}$-alkyl sulfanyl, $C_1$-$C_{12}$-alkyl sulfonylamino, or $C_1$-$C_{12}$-alkyl aminosulfonyl, and preferably with at least one or $R^1$ and $R^2$ being other than hydrogen;

$R^3$ is $C_1$-$C_{16}$-alkyl, $C_2$-$C_{16}$-alkenyl, $C_2$-$C_{16}$-alkynyl, wherein said alkyl, alkenyl, alkynyl chains may be interrupted by a heteroatom selected from N, O or S, aryl, heteroaryl, saturated or unsaturated 3-8-membered cycloalkyl, heterocycloalkyl, wherein said cycloalkyl, heterocycloalkyl, aryl or heteroaryl groups may be fused with 1-2 further cycloalkyl, heterocycloalkyl, aryl or heteroaryl group, an acyl moiety, $C_1$-$C_{16}$-alkyl aryl, $C_1$-$C_{16}$-alkyl heteroaryl, $C_2$-$C_{16}$-alkenyl aryl, $C_2$-$C_{16}$-alkenyl heteroaryl, $C_2$-$C_{16}$-alkynyl aryl, $C_2$-$C_{16}$-alkynyl heteroaryl, $C_1$-$C_{16}$-alkyl cycloalkyl, $C_1$-$C_{16}$-alkyl heterocycloalkyl, $C_2$-$C_{16}$-alkenyl cycloalkyl, $C_2$-$C_{16}$-alkenyl heterocycloalkyl, $C_2$-$C_{16}$-alkynyl cycloalkyl, $C_2$-$C_{16}$-alkynyl heterocycloalkyl, alkoxycarbonyl, aminocarbonyl, $C_1$-$C_{16}$-alkyl carboxy, $C_1$-$C_{16}$-alkyl acyl, aryl acyl, heteroaryl acyl, $C_3$-$C_8$-(hetero)cycloalkyl acyl, $C_1$-$C_{16}$-alkyl acyloxy, $C_1$-$C_{16}$-alkyl alkoxy, $C_1$-$C_{16}$-alkyl alkoxycarbonyl, $C_1$-$C_{16}$-alkyl aminocarbonyl, $C_1$-$C_{16}$-alkyl acylamino, acylamino, $C_1$-$C_{16}$-alkyl ureido, $C_1$-$C_{16}$-alkyl carbamate, $C_1$-$C_{16}$-alkyl amino, $C_1$-$C_{16}$-alkyl ammonium, $C_1$-$C_{16}$-alkyl sulfonyloxy, $C_1$-$C_{16}$-alkyl sulfonyl, $C_1$-$C_{16}$-alkyl sulfinyl, $C_1$-$C_{16}$-alkyl sulfanyl, $C_1$-$C_{16}$-alkyl sulfonylamino, or $C_1$-$C_{16}$-alkyl aminosulfonyl;

$R^4$ is $C_1$-$C_{12}$-alkyl, $C_2$-$C_{12}$-alkenyl, $C_2$-$C_{12}$-alkynyl, wherein said alkyl, alkenyl, alkynyl chains may be interrupted by a heteroatom selected from N, O or S, aryl, heteroaryl, saturated or unsaturated 3-8-membered cycloalkyl, heterocycloalkyl, wherein said cycloalkyl, heterocycloalkyl, aryl or heteroaryl groups may be fused with 1-2 further cycloalkyl, heterocycloalkyl, aryl or heteroaryl group or amino group; and pharmaceutically acceptable salts thereof.

Generally preferred compounds of the invention include those where the substituent $R^4$ of Formula I is heteroaryl, particularly a sulfur-ring substituent especially such as compounds of the following Formula II:

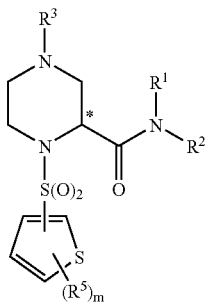

II wherein $R^1$, $R^2$ and $R^3$ are the same as defined above in Formula I;

each $R^5$ is independently halogen, hydroxy or the same as defined for $R^1$;

m is an integer of from 0 (where available thienyl ring positions are hydrogen-substituted) to 4, and preferably m is 0, 1, 2 or 3, more preferably 0, 1 or 2; and pharmaceutically acceptable salts thereof.

Compounds of Formula II having a 2-thienyl moiety are typically preferred, i.e. compounds of the following Formula III:

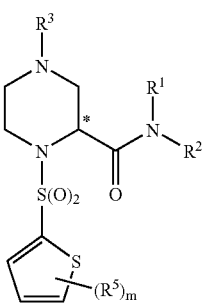

III wherein $R^1$, $R^2$, $R^3$, $R^5$ and m are the same as defined for Formula II above; and pharmaceutically acceptable salts thereof.

As mentioned above, in each of Formulae I through III, preferably at least one of $R^1$ and $R^2$ is other than hydrogen, and more preferably, one of $R^1$ and $R^2$ is hydrogen and the other a non-hydrogen substituent. Preferred non-hydrogen $R^1$ and $R^2$ substituents include optionally substituted aryl and optionally substituted heteroaryl groups such as optionally substituted phenyl, naphthyl, pyridyl, and fused aryl and heteroaryl ring systems such as benzoimidazole, pyridyl-substituted benzoimidazole, carbazole and the like. Especially preferred non-hydrogen $R^1$ and $R^2$ substituents include those that comprise an optionally substituted carbazolyl, an optionally substituted tetrahydro-beta-carbolinyl or an optionally substituted benzimidazolyl moiety, such as a 1-benzimidazolyl which may be N-substituted by $C_1$-$C_8$ alkyl, 2,3,4,9-tetrahydro-beta-carbolin-6yl-1-one and 9-ethyl-9H-carbazol-3yl or the like.

In Formulae I through III, preferred $R^3$ groups contain 4 or more atoms, particularly in a sequential chain, even more preferably 5, 6, 7, 8, 9, or 10 atoms in an extended chain such as an alkyl chain or ester, amide or other moiety. Alkyl groups, including n-alkyl groups, that contain 4, 5, 6, 7, 8, 9 or 10 carbon atoms are particularly preferred $R^3$ substituents.

A preferred embodiment of the invention, is a piperazine derivative according to Formula I wherein $R^1$ is H; $R^2$ is selected from optionally substituted aryl, optionally substituted heteroaryl, optionally substituted saturated or unsaturated 3-8-membered cycloalkyl and optionally substituted heterocycloalkyl, wherein said cycloalkyl, heterocycloalkyl, aryl or heteroaryl groups may be fused with 1-2 further cycloalkyl, heterocycloalkyl, aryl or heteroaryl group; $R^3$ is selected from optionally substituted $C_1$-$C_{16}$-alkyl, optionally substituted $C_2$-$C_{16}$-alkenyl, optionally substituted $C_2$-$C_{16}$-alkynyl, wherein said alkyl, alkenyl, alkynyl chains may be interrupted by a heteroatom selected from N and O, optionally substituted monocyclic aryl, optionally substituted monocyclic heteroaryl, optionally substituted saturated or optionally substituted unsaturated 3-8-membered monocyclic cycloalkyl, optionally substituted monocyclic heterocycloalkyl, an acyl moiety, optionally substituted $C_1$-$C_{16}$-alkyl aryl, optionally substituted $C_1$-$C_{16}$-alkyl heteroaryl, optionally substituted $C_2$-$C_{16}$-alkenyl aryl, optionally substituted $C_2$-$C_{16}$-alkenyl heteroaryl, optionally substituted $C_2$-$C_{16}$-alkynyl aryl, optionally substituted $C_2$-$C_{16}$-alkynyl heteroaryl, optionally substituted $C_1$-$C_{16}$-alkyl cycloalkyl, optionally substituted $C_1$-$C_{16}$-alkyl heterocycloalkyl, optionally substituted $C_2$-$C_{16}$-alkenyl cycloalkyl, optionally substituted $C_2$-$C_{16}$-alkenyl heterocycloalkyl, optionally substituted $C_2$-$C_{16}$-alkynyl cycloalkyl, optionally substituted $C_2$-$C_{16}$-alkynyl heterocycloalkyl, optionally substituted alkoxycarbonyl, optionally substituted aminocarbonyl, optionally substituted $C_1$-$C_{16}$-alkyl carboxy, optionally substituted $C_1$-$C_{16}$-alkyl acyl, optionally substituted aryl acyl, optionally substituted heteroaryl acyl, optionally substituted $C_3$-$C_8$-(hetero)cycloalkyl acyl, optionally substituted $C_1$-$C_{16}$-alkyl acyloxy, optionally substituted $C_1$-$C_{16}$-alkyl alkoxy, optionally substituted $C_1$-$C_{16}$-alkyl alkoxycarbonyl, optionally substituted $C_1$-$C_{16}$-alkyl aminocarbonyl, optionally substituted $C_1$-$C_{16}$-alkyl acylamino, optionally substituted acylamino, optionally substituted $C_1$-$C_{16}$-alkyl sulfinyl, optionally substituted $C_1$-$C_{16}$-alkyl sulfanyl, optionally substituted $C_1$-$C_{16}$-alkyl ureido, optionally substituted $C_1$-$C_{16}$-alkyl carbamate, optionally substituted $C_1$-$C_{16}$-alkyl amino and optionally substituted $C_1$-$C_{16}$-alkyl ammonium; $R^4$ is selected from optionally substituted $C_1$-$C_{12}$-alkyl, optionally substituted $C_2$-$C_{12}$-alkenyl, optionally substituted $C_2$-$C_{12}$-alkynyl, wherein said alkyl, alkenyl, alkynyl chains may be interrupted by a heteroatom selected from N, O and S, optionally substituted aryl, optionally substituted heteroaryl, saturated or unsaturated 3-8-membered cycloalkyl, heterocycloalkyl, wherein said cycloalkyl, heterocycloalkyl, aryl or heteroaryl groups may be fused with 1-2 further cycloalkyl, heterocycloalkyl, aryl or heteroaryl group, and optionally substituted amino group.

A particularly preferred embodiment, is a piperazine derivative according to Formulae I to III wherein $R^1$ is H and $R^2$ is selected from optionally substituted aryl and optionally substituted heteroaryl, wherein optionally substituted aryl and optionally substituted heteroaryl can be optionally polycyclic and include optionally substituted phenyl, optionally substituted benzimidazolyl, optionally substituted carbazolyl and optionally substituted tetrahydro carbolinyl.

A further preferred embodiment, is a piperazine derivative according to Formulae I to III, wherein $R^1$ is H and $R^2$ is selected from optionally substituted aryl and optionally substituted heteroaryl, wherein optionally substituted aryl and optionally substituted heteroaryl are bi-cyclic or tricyclic and include optionally substituted benzimidazolyl, optionally substituted carbazolyl and optionally substituted tetrahydro carbolinyl.

A particularly preferred embodiment, is a piperazine derivative according to Formulae I to III, wherein $R^1$ is H and $R^3$ is selected from optionally substituted $C_1$-$C_8$-alkyl, including pentyl, hexyl, heptyl and octyl; optionally substituted $C_1$-$C_8$-alkyl acyloxy, including acetic acid ethyl ester; optionally substituted $C_1$-$C_8$-alkyl sulfanyl, including methylsulfanyl propyl; optionally substituted $C_1$-$C_8$-alkyl heteroaryl, including imidazolyl propyl and ethyl furanylmethyl; optionally substituted aminocarbonyl, including ethoxy ethyl formamide, formylamino-acetic acid ethyl ester and imidazolyl propylamide; optionally substituted $C_1$-$C_8$-alkyl aminocarbonyl, including ethylamide and pentylamide and optionally substituted carbonyl, including pentanoyl.

A further preferred embodiment, is a piperazine derivative according to Formulae I to III, wherein $R^1$ is H and $R^3$ is selected from optionally substituted $C_1$-$C_8$-alkyl, including pentyl, hexyl, heptyl and octyl and optionally substituted $C_1$-$C_8$-alkyl aminocarbonyl, including ethylamide and pentylamide.

A particularly preferred embodiment, is a piperazine derivative according to Formula I wherein $R^1$ is H and $R^4$ is selected from optionally substituted $C_1$-$C_6$-alkyl, wherein said alkyl chain may be interrupted by a nitrogen atom, including butane; optionally substituted amino group, including dimethyl amine; optionally substituted aryl, including optionally substituted phenyl such as phenyl and fluorophenyl; optionally substituted heteroaryl, including thienyl and methyl imidazole.

A further preferred embodiment, is a piperazine derivative according to Formula I wherein $R^1$ is H and $R^4$ is selected from optionally substituted aryl, including optionally substituted phenyl such as fluorophenyl; optionally substituted heteroaryl, including thiophene and methyl imidazole.

Generally preferred $R^4$ substituents of Formula I are optionally substituted alkyl, optionally substituted aryl and optionally substituted heteroaryl groups, such as optionally substituted $C_{1-12}$ alkyl, optionally substituted aryl such as optionally substituted phenyl e.g. phenyl having one or more ring substituents of halogen, nitro, $C_1$-$C_6$ alkyl, $C_{1-6}$ alkoxy, and the like, and optionally substituted heteroaryl, particularly thiophene and furane.

The invention also includes compounds and use of optically active compounds of the above Formulae I through III, particularly compounds of the above Formulae I through III where a single stereoisomer of a chiral compound is present in an enantiomeric excess, e.g. where a single stereoisomer is present in an amount of at least 70 mole percent relative to other stereoisomer(s), more preferably where one stereoisomer is present in an amount of at least about 80, 85, 90, 92, 93, 94, 95, 96, 97, 98 or 99 mole percent relative to other stereoisomer(s). Particularly preferred is where a stereoisomer of the depicted chiral carbon (i.e. the chiral piperazine ring carbon indicated by * in each Formulae I, II and III) is present in an enantiomeric excess, such as the amounts specified above relative to other stereoisomer(s).

Carboxamide piperazine compounds of the invention are useful for treatment of infertility in male and female mammals, particularly humans. Therapeutic methods of the invention in general comprise administering an effective amount of one or more 2-carboxamide piperazine compounds as disclosed herein to a mammal in need thereof, such as a mammal suspected of suffering from infertility, particularly a human suspected of suffering from infertility. Compounds of the invention will be useful for treatment of infertility conditions currently treated with FSH and/or LH, including female infertility and male spermatogenesis disorders.

Additionally, in contrast to current protein therapeutics such as FSH, compounds of the invention can be administered orally and without extensive medical specialist supervision.

Preferred compounds of the invention exhibit good agonist activity in standard Follicle Stimulating Hormone (FSH) assays, such as the assay of Example 2 which follows.

It also has been found that 2-carboxamide piperazine compounds of the invention exhibit good inhibition activity against phosphodiesterase PDE4, adenosine transporters, and prostanoid receptors. Accordingly, methods are provided for treatment of diseases and disorders associated with phosphodiesterase PDE4, adenosine transporters, and prostanoid receptors, which methods in general comprise administration of an effective amount of one or more 2-carboxamide piperazine compounds to a patient (e.g. mammal, such as human or other primate) in need of such treatment.

In a further aspect, the invention provides a use of a carboxamide piperazine compound as disclosed herein, particularly a compound of any one of Formulae I through m for the treatment or prevention (including prophylactic treatment) of a disease or condition as disclosed herein, including treatment of infertility in male and female mammals, particularly humans, such as female infertility and male spermatogenesis disorders, as well as treatment of diseases and disorders associated with phosphodiesterase PDE4, adenosine transporters, and prostanoid receptors.

In a yet further aspect, the invention provides use of a carboxamide piperazine compound as disclosed herein, particularly a compound of any one of Formulae I through III, for the preparation of a medicament for the treatment or prevention (including prophylactic treatment) of a disease or condition as disclosed herein, including treatment of infertility in male and female mammals, particularly humans, such as female infertility and male spermatogenesis disorders, as well as treatment of diseases and disorders associated with phosphodiesterase PDE4, adenosine transporters, and prostanoid receptors.

Preferred methods of the invention including identifying and/or selecting a subject (e.g. mammal, particularly human) that is susceptible or suffering from a condition disclosed herein, and thereafter administering to the identified and selected subject one or more carboxamide piperazine compounds of the invention, particularly a subject that is identified and selected as being susceptible to or suffering from infertility, such as female infertility and male spermatogenesis disorders in humans, as well as subjects susceptible to or suffering from a disease or disorder associated with phosphodiesterase PDE4, adenosine transporters, and prostanoid receptors.

The invention also provides pharmaceutical compositions that comprise one or more 2-carboxamide piperazine compounds of the invention and a suitable carrier for the compositions. Other aspects of the invention are disclosed infra.

DETAILED DESCRIPTION OF THE INVENTION

We have now discovered that substituted carboxamide piperazine compounds, including compounds of the above Formulae I, II and III, that are useful for treatment of infertility in mammals, including female and male humans.

The following paragraphs provide definitions of the various chemical moieties that make up the compounds according to the invention and are intended to apply uniformly through-out the specification and claims, unless an otherwise expressly set out definition provides a broader definition.

"$C_1$-$C_{12}$-alkyl" refers to monovalent alkyl groups having 1 to 12 carbon atoms. This term is exemplified by groups such as methyl, ethyl, n-propyl, isopropyl, n-butyl, isobutyl, tertt-butyl, n-hexyl and the like. By analogy, "$C_1$-$C_{16}$-alkyl" refers to monovalent alkyl groups having 1 to 16 carbon atoms, "$C_1$-$C_8$-alkyl" refers to monovalent alkyl groups having 1 to 8 carbon atoms and "$C_1$-$C_6$-alkyl" refers to monovalent alkyl groups having 1 to 6 carbon atoms.

"Aryl" refers to an unsaturated aromatic carbocyclic group of from 6 to 14 carbon atoms having a single ring or "monocyclic ring" (e.g., phenyl), multiple condensed rings or "polycyclic ring", including for example "bi-cyclic" ring (e.g., naphthyl), "tri-cyclic" ring (e.g. 9-carbazolyl) or other linked multiple rings (e.g. bi-phenyl). Preferred aryl include phenyl, naphthyl, anthracenyl, acenaphthyl, phenanthrenyl and the like. The expression "fused aryl" means an aryl that is fused with further cycloalkyl, heterocycloalkyl, aryl or heteroaryl group(s), preferably 1 or 2.

"$C_1$-$C_{12}$-alkyl aryl" refers to $C_1$-$C_{12}$-alkyl groups having an aryl substituent, including benzyl, phenethyl and the like. By analogy, "$C_1$-$C_{16}$-alkyl aryl" refers to $C_1$-$C_{16}$-alkyl groups having an aryl substituent and "$C_1$-$C_8$-alkyl aryl" refers to $C_1$-$C_8$-alkyl groups having an aryl substituent.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, benzoxazole, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_{12}$-alkyl heteroaryl" refers to $C_1$-$C_{12}$-alkyl groups having a heteroaryl substituent, including 2-furylmethyl, 2-thienylmethyl, 2-(1H-indol-3-yl)ethyl and the like. By analogy, "$C_1$-$C_{16}$-alkyl heteroaryl" refers to $C_1$-$C_{16}$-alkyl groups having a heteroaryl substituent and "$C_1$-$C_8$-alkyl heteroaryl" refers to $C_1$-$C_8$-alkyl groups having an heteroaryl substituent.

"$C_2$-$C_{12}$-alkenyl" refers to alkenyl groups preferably having from 2 to 12 carbon atoms and having at least 1 or 2 sites of alkenyl unsaturation. By analogy, "$C_2$-$C_{16}$-alkenyl" refers to alkenyl groups preferably having from 2 to 16 carbon atoms and having at least 1 or 2 sites of alkenyl unsaturation Preferable alkenyl groups include ethenyl (—CH═CH$_2$), n-2-propenyl (allyl, —CH$_2$CH═CH$_2$) and the like.

"$C_2$-$C_{12}$-alkenyl aryl" refers to $C_2$-$C_{12}$-alkenyl groups having an aryl substituent, including 2-phenylvinyl and the like. By analogy, "$C_2$-$C_{16}$-alkenyl aryl" refers to $C_2$-$C_{16}$-alkenyl groups having an aryl substituent "$C_2$-$C_{12}$-alkenyl heteroaryl" refers to $C_2$-$C_{12}$-alkenyl groups having a heteroaryl substituent, including 2-(3-pyridinyl)vinyl and the like. By analogy, "$C_2$-$C_{16}$-alkenyl heteroaryl" refers to $C_2$-$C_{16}$-alkenyl groups having a heteroaryl substituent "$C_2$-$C_{12}$-alkynyl" refers to alkynyl groups preferably having from 2 to 12 carbon atoms and having at least 1-2 sites of alkynyl unsaturation. By analogy, "$C_2$-$C_{16}$-alkynyl" refers to alkynyl groups preferably having from 2 to 16 carbon atoms and having at least 1-2 sites of alkynyl unsaturation. Preferred alkynyl groups include ethynyl (—C≡CH), propargyl (—CH$_2$C≡CH), and the like.

"$C_2$-$C_{12}$-alkynyl aryl" refers to $C_2$-$C_{12}$-alkynyl groups having an aryl substituent, including phenylethynyl and the like. By analogy, "$C_2$-$C_{16}$-alkynyl aryl" refers to $C_2$-$C_{16}$-alkynyl groups having an aryl substituent.

"$C_2$-$C_{12}$-alkynyl heteroaryl" refers to $C_2$-$C_{12}$-alkynyl groups having a heteroaryl substituent, including 2-thienylethynyl and the like. By analogy, "$C_2$-$C_{16}$-alkynyl heteroaryl" refers to $C_2$-$C_{16}$-alkynyl groups having a heteroaryl substituent "$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen, $C_{1-6}$ alkyl, alkoxy and the like. thyl. Preferred heterocycloalkyl include pyrrolidine, piperidine, piperazine, 1-methylpiperazine, morpholine, and the like.

"$C_1$-$C_{12}$-alkyl cycloalkyl" refers to $C_1$-$C_{12}$-alkyl groups having a cycloalkyl substituent, including cyclohexylmethyl, cyclopentylpropyl, and the like. By analogy, "$C_1$-$C_{16}$-alkyl cycloalkyl" refers to $C_1$-$C_{16}$-alkyl groups having a cycloalkyl substituent "$C_1$-$C_{12}$-alkyl heterocycloalkyl" refers to $C_1$-$C_{12}$-alkyl groups having a heterocycloalkyl substituent, including 2-(1-pyrrolidinyl)ethyl, 4-morpholinylmethyl, (1-methyl-4-piperidinyl)methyl and the like. By analogy, "$C_1$-$C_{16}$-alkyl heterocycloalkyl" refers to $C_1$-$C_{16}$-alkyl groups having a heterocycloalkyl substituent "Carboxy" refers to the group —C(O)OH.

"$C_1$-$C_{12}$-alkyl carboxy" refers to $C_1$-$C_{12}$-alkyl groups having a carboxy substituent, including 2-carboxyethyl and the like. By analogy, "$C_1$-$C_{16}$-alkyl carboxy" refers to $C_1$-$C_{16}$-alkyl groups having a carboxy substituent "Acyl" refers to the group —C(O)R where R includes "$C_1$-$C_{12}$-alkyl", "$C_1$-$C_8$-alkyl", "aryl", "heteroaryl", "$C_1$-$C_{12}$-alkyl aryl" or "$C_1$-$C_{12}$-alkyl heteroaryl".

"$C_1$-$C_{12}$-alkyl acyl" refers to $C_1$-$C_{12}$-alkyl groups having an acyl substituent, including 2-acetylethyl and the like. By analogy, "$C_1$-$C_{16}$-alkyl acyl" refers to $C_1$-$C_{16}$-alkyl groups having an acyl substituent "Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_{12}$-alkyl", "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl".

"$C_1$-$C_{12}$-alkyl acyloxy" refers to $C_1$-$C_{12}$-alkyl groups having an acyloxy substituent, including 2-(acetyloxy)ethyl and the like. By analogy, "$C_1$-$C_{16}$-alkyl acyloxy" refers to $C_1$-$C_{16}$-alkyl groups having an acyloxy substituent "Alkoxy" refers to the group —O—R where R includes "$C_1$-$C_{12}$-alkyl", "$C_1$-$C_8$-alkyl", "$C_1$-$C_6$-alkyl" or "aryl" or "hetero-aryl" or "$C_1$-$C_{12}$-alkyl aryl" or "$C_1$-$C_{12}$-alkyl heteroaryl". Preferred alkoxy groups include by way of example, methoxy, ethoxy, phenoxy and the like.

"$C_1$-$C_{12}$-alkyl alkoxy" refers to $C_1$-$C_{12}$-alkyl groups having an alkoxy substituent, including 2-ethoxyethyl and the like. By analogy, "$C_1$-$C_{16}$-alkyl alkoxy" refers to $C_1$-$C_{16}$-alkyl groups having an alkoxy substituent and "$C_1$-$C_6$-alkyl" refers to $C_1$-$C_6$-alkyl groups having an alkoxy substituent "Alkoxycarbonyl" refers to the group —C(O)OR where R includes H, "$C_1$-$C_{12}$-alkyl" or "aryl" or "heteroaryl" or "$C_1$-$C_{12}$-alkyl aryl" or "$C_1$-$C_{12}$-alkyl heteroaryl".

"$C_1$-$C_{12}$-alkyl alkoxycarbonyl" refers to $C_1$-$C_{12}$-alkyl groups having an alkoxycarbonyl substituent, including 2-(benzyloxycarbonyl)ethyl and the like. By analogy, "$C_1$-$C_{16}$-alkyl alkoxycarbonyl" refers to $C_1$-$C_{16}$-alkyl groups having an alkoxycarbonyl substituent "Aminocarbonyl" refers to the group —C(O)NRR' where each R, R' includes independently hydrogen or $C_1$-$C_{12}$-alkyl or $C_1$-$C_6$-alkyl or aryl or heteroaryl or "$C_1$-$C_{12}$-alkyl aryl" or "$C_1$-$C_{12}$-alkyl hetero-aryl".

"$C_1$-$C_{12}$-alkyl aminocarbonyl" refers to $C_1$-$C_{12}$-alkyl groups having an aminocarbonyl substituent, including 2-(dimethylaminocarbonyl)ethyl and the like. By analogy, "$C_1$-$C_{16}$-alkyl aminocarbonyl" refers to $C_1$-$C_{16}$-alkyl groups having an aminocarbonyl substituent and "$C_1$-$C_8$-alkyl aminocarbonyl" refers to $C_1$-$C_8$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_{12}$-alkyl", "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl".

"$C_1$-$C_{12}$-alkyl acylamino" refers to $C_1$-$C_{12}$-alkyl groups having an acylamino substituent, including 2-(propionylamino)ethyl and the like. By analogy, "$C_{1-16}$-alkyl acylamino" refers to $C_1$-$C_{16}$-alkyl groups having an acylamino substituent "Ureido" refers to the group —NRC(O)NR'R" where each R, R', R" is independently hydrogen, "$C_1$-$C_{12}$-alkyl", "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl", and where R' and R", together with the nitrogen atom to which they are attached, can optionally form a 3-8-membered heterocycloalkyl ring.

"$C_1$-$C_{12}$-alkyl ureido" refers to $C_1$-$C_{12}$-alkyl groups having an ureido substituent, including 2-(N'-methylureido)ethyl and the like. By analogy, "$C_1$-$C_{16}$-alkyl ureido" refers to $C_1$-$C_{16}$-alkyl groups having an ureido substituent "Carbamate" refers to the group —NRC(O)OR' where each R, R' is independently hydrogen, "$C_1$-$C_{12}$-alkyl", "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl".

"Amino" refers to the group —NRR' where each R,R' is independently hydrogen or "$C_1$-$C_{12}$-alkyl" or "aryl" or "heteroaryl" or "$C_1$-$C_2$-alkyl aryl" or "$C_1$-$C_{12}$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_{12}$-alkyl amino" refers to $C_1$-$C_{12}$-alkyl groups having an amino substituent, including 2-(1-pyrrolidinyl)ethyl and the like. By analogy, "$C_1$-$C_{16}$-alkyl amino" refers to $C_1$-$C_{16}$-alkyl groups having an amino substituent and "$C_1$-$C_8$-alkyl amino" refers to $C_1$-$C_8$-alkyl groups having an amino substituent "Ammonium" refers to a positively charged group —$N^+$RR'R", where each R,R',R" is independently "$C_1$-$C_{12}$-alkyl" or "$C_1$-$C_{12}$-alkyl aryl" or "$C_1$-$C_{12}$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_{12}$-alkyl ammonium" refers to $C_1$-$C_{12}$-alkyl groups having an ammonium substituent, including 2-(1-pyrrolidinyl)ethyl and the like. By analogy, "$C_1$-$C_{16}$-alkyl ammonium" refers to $C_1$-$C_{16}$-alkyl groups having an ammonium substituent.

"Halogen" refers to fluoro, chloro, bromo and iodo atoms.

"Sulfonyloxy" refers to a group —OSO$_2$—R wherein R is selected from H, "$C_1$-$C_{12}$-alkyl", "$C_1$-$C_{12}$-alkyl" substituted with halogens, e.g., an —OSO$_2$—CF$_3$ group, "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_6$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl".

"$C_1$-$C_{12}$-alkyl sulfonyloxy" refers to $C_1$-$C_{12}$-alkyl groups having a sulfonyloxy substituent, including 2-(methylsulfonyloxy)ethyl and the like. By analogy, "$C_1$-$C_{16}$-alkyl sulfonyloxy" refers to $C_1$-$C_{16}$-alkyl groups having a sulfonyloxy substituent "Sulfonyl" refers to group "—SO$_2$—R" wherein R is selected from H, "aryl", "heteroaryl", "$C_1$-$C_{12}$-alkyl", "$C_1$-$C_{12}$-alkyl" substituted with halogens, e.g., an —SO$_2$—CF$_3$ group, "$C_2$-$C_6$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "$C_2$-$C_{12}$-alkynyl aryl", "$C_2$-$C_{12}$-alkynylheteroaryl", "$C_1$-$C_{12}$-alkyl cycloalkyl", "$C_1$-$C_{12}$-alkyl heterocycloalkyl".

"$C_1$-$C_{12}$-alkyl sulfonyl" refers to $C_1$-$C_{12}$-alkyl groups having a sulfonyl substituent, including 2-(methylsulfonyl)ethyl and the like. By analogy, "$C_1$-$C_{16}$-alkyl sulfonyl" refers to $C_1$-$C_{16}$-alkyl groups having a sulfonyl substituent.

"Sulfinyl" refers to a group "—S(O)—R" wherein R is selected from H, "$C_1$-$C_{12}$-alkyl", "$C_1$-$C_6$-alkyl" substituted with halogens, e.g., an —SO—CF$_3$ group, "$C_2$-$C_{12}$-alkenyl", "$C_2$-$C_{12}$-alkynyl", "$C_3$-$C_8$-cycloalkyl", "heterocycloalkyl", "aryl", "heteroaryl", "$C_1$-$C_{12}$-alkyl aryl" or "$C_1$-$C_{12}$-alkyl heteroaryl", "$C_2$-$C_{12}$-alkenyl aryl", "$C_2$-$C_{12}$-alkenyl heteroaryl", "C₂-C₁₂-alkynyl aryl", "C₂-C₁₂-alkynylheteroaryl", "C₁-C₁₂-alkyl cycloalkyl", "C₁-C₁₂-alkyl heterocycloalkyl".

"C₁-C₁₂-alkyl sulfinyl" refers to C₁-C₁₂-alkyl groups having a sulfinyl substituent, including 2-(methylsulfinyl)ethyl and the like. By analogy, "C₁-C₁₆-alkyl sulfinyl" refers to C₁-C₁₆-alkyl groups having a sulfinyl substituent.

"Sulfanyl" refers to groups —S—R where R includes H, "C₁-C₁₂-alkyl", "C₁-C₁₂-alkyl" substituted with halogens, e.g., a —SO—CF₃ group, "C₂-C₁₂-alkenyl", "C₂-C₁₂-alkynyl", "C₃-C₈-cycloalkyl", "heterocycloalkyl", "aryl", "heteroaryl", "C₁-C₁₂-alkyl aryl" or "C₁-C₆-alkyl heteroaryl", "C₂-C₁₂-alkenyl aryl", "C₂-C₁₂-alkenyl heteroaryl", "C₂-C₁₂-alkynyl aryl", "C₂-C₁₂-alkynylheteroaryl", "C₁-C₁₂-alkyl cycloalkyl", "C₁-C₁₂-alkyl heterocycloalkyl". Preferred sulfanyl groups include methylsulfanyl, ethylsulfanyl, and the like.

"C₁-C₁₂-alkyl sulfanyl" refers to C₁-C₁₂-alkyl groups having a sulfanyl substituent, including 2-(ethylsulfanyl)ethyl and the like. By analogy, "C₁-C₁₆-alkyl sulfanyl" refers to C₁-C₁₆-alkyl groups having a sulfanyl substituent.

"Sulfonylamino" refers to a group —NRSO₂—R' where each R, R' includes independently hydrogen, "C₁-C₁₂-alkyl", "C₂-C₁₂-alkenyl", "C₂-C₁₂-alkynyl", "C₃-C₈-cycloalkyl", "heterocycloalkyl", "aryl", "heteroaryl", "C₁-C₁₂-alkyl aryl" or "C₁-C₁₂-alkyl heteroaryl", "C₂-C₁₂-alkenyl aryl", "C₂-C₁₂-alkenyl heteroaryl", "C₂-C₁₂-alkynyl aryl", "C₂-C₁₂-alkynylheteroaryl", "C₁-C₁₂-alkyl cycloalkyl", "C₁-C₁₂-alkyl heterocycloalkyl".

"C₁-C₁₂-alkyl sulfonylamino" refers to C₁-C₁₂-alkyl groups having a sulfonylamino substituent, including 2-(ethylsulfonylamino)ethyl and the like. By analogy, "C₁-C₁₆-alkyl sulfonylamino" refers to C₁-C₁₆-alkyl groups having a sulfonylamino substituent.

"Aminosulfonyl" refers to a group —SO₂—NRR' where each R, R' includes independently hydrogen, "C₁-C₁₂-alkyl", "C₂-C₁₂-alkenyl", "C₂-C₁₂-alkynyl", "C₃-C₈-cycloalkyl", "heterocycloalkyl", "aryl", "heteroaryl", "C₁-C₁₂-alkyl aryl" or "C₁-C₁₂-alkyl heteroaryl", "C₂-C₁₂-alkenyl aryl", "C₂-C₁₂-alkenyl heteroaryl", "C₂-C₁₂-alkynyl aryl", "C₂-C₁₂-alkynylheteroaryl", "C₁-C₁₂-alkyl cycloalkyl", "C₁-C₁₂-alkyl heterocycloalkyl".

"C₁-C₁₂-alkyl aminosulfonyl" refers to C₁-C₁₂-alkyl groups having an aminosulfonyl substituent, including 2-(cyclohexylaminosulfonyl)ethyl and the like. By analogy, "C₁-C₁₆-alkyl aminosulfonyl" refers to C₁-C₁₆-alkyl groups having an aminosulfonyl substituent.

"Substituted or unsubstituted" or "optionally substituted: Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C₁-C₁₂-alkyl", "C₂-C₁₂-alkenyl", "C₂-C₁₂-alkynyl", "cycloalkyl", "heterocycloalkyl", "C₁-C₁₂-alkyl aryl", "C₁-C₁₂-alkyl heteroaryl", "C₁-C₁₂-alkyl cycloalkyl", "C₁-C₁₂-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactone, cyclic anhydrides, but also acetals, thioacetals, aminals formed by ring closure for instance in an effort to obtain a protective group.

Specifically, preferred compounds of the invention include the following compounds, and pharmaceutically acceptable salts of these compounds, with the compound name set forth above the depicted compound structure. The structurally depicted compounds generally show preferred stereoisomers.

4-hexyl-1-(thiophene-2-sulfonyl)-piperazine-2-carboxylic acid (1-ethyl-2-pyridinyl-3-yl-1H-benzoimidazole-5-yl)-amide

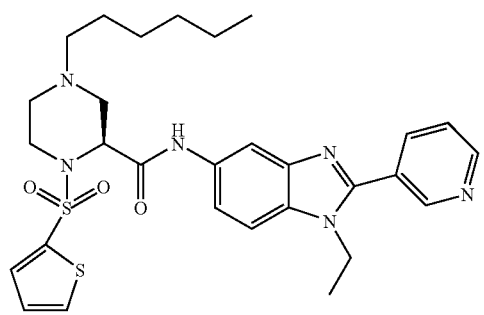

4-pentanoyl-1-(thiophene-2-sulfonyl)-piperazine-2-carboxylic acid (9-ethyl-9H-carbazol-3-yl) amide

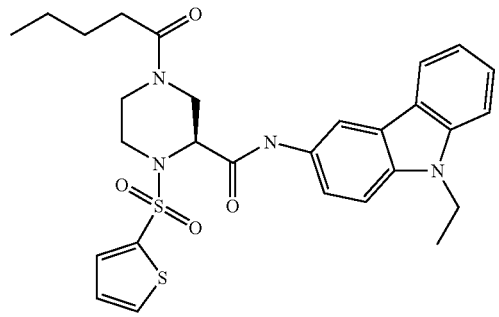

{[3-(9-ethyl-9H-carbazol-3-ylcarbamoyl)-4-(thiophene-2-sulfonyl)-piperazine-1-carbonyl]-amino}acetic acid ethyl ester

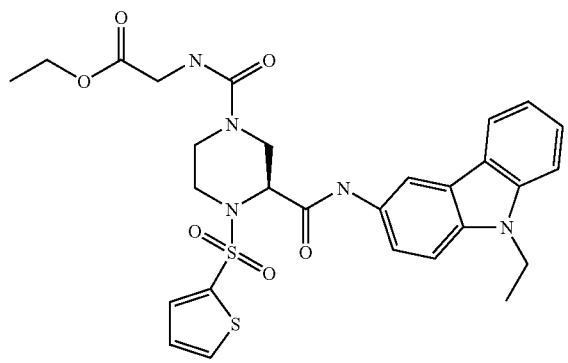

13

4-(thiophene-2-sulfonyl)-piperazine-1,3-dicarboxylic acid 1-ethylamide 3-[(9-ethyl-9H-carbazol-3-yl) amide]

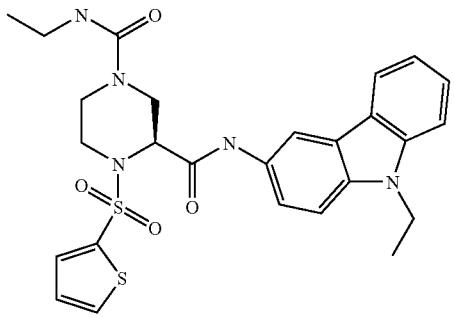

4-(thiophene-2-sulfonyl)-piperazine-1,3-dicarboxylic acid 3-[(9-ethyl-9H-carbazol-3-yl)amide]-1-pentylamide

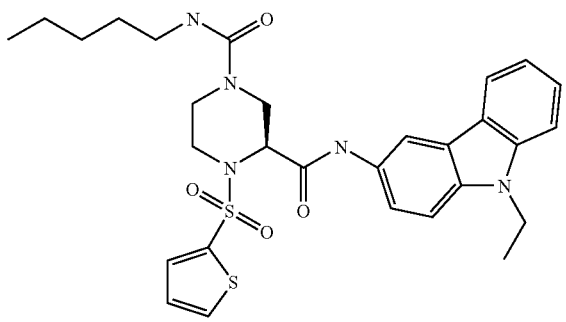

4-hexyl-1-(thiophene-2-sulfonyl)-piperazine-2-carboxylic acid (9-ethyl-9H-carbazol-3-yl) amide

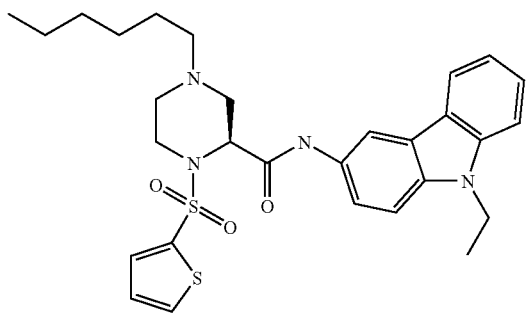

14

4-(thiophene-2-sulfonyl)-piperazine-1,3-dicarboxylic acid 3-[(9-ethyl-9H-carbazol-3-yl)-amide]1-{(2-methoxy-ethyl)-amide]

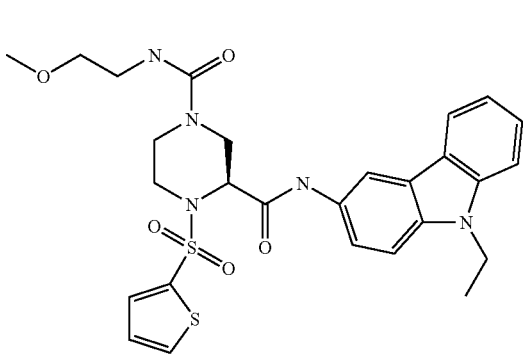

4-(thiophene-2-sulfonyl)-piperazine-1,3-dicarboxyclic acid 1-pentylamide 3-[(3-pyridin-4-yl-phenyl)-amide]

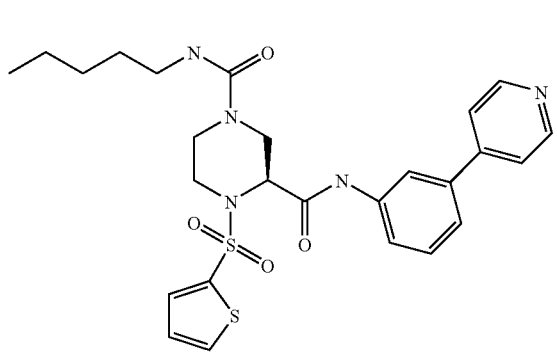

4-(1-methyl-1H-imidazole-4-sulfonyl)-piperazine-1,3-dicarboxylic acid 3-[(9-ethyl-9H-carbazol-3-yl)-amide]1-pentylamide

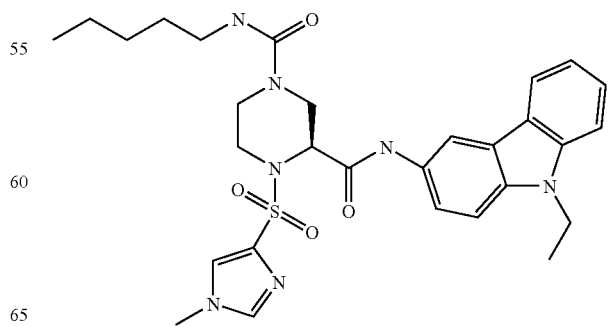

| 15 | 16 |
|---|---|
| 4-dimethylsulfamoyl-piperazine-1,3-dicarboxylic acid 3-[(9-ethyl-9H-carbazol-3-yl)-amide]1-pentylamide | 4-(thiophene-2-sulfonyl)-piperazine-1,3-dicarboxylic acid 3-[(9-ethyl-9H-carbazol-3-yl)-amide]1-[(3-imidazol-1-yl-propyl)-amide]) |

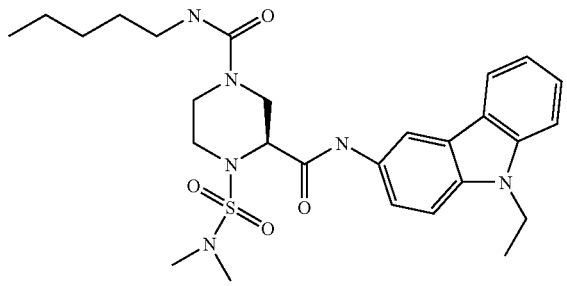

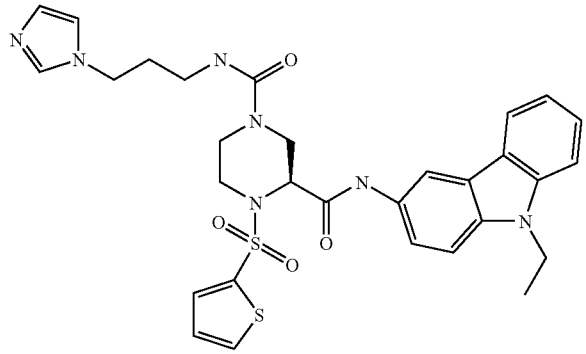

4-hexyl-1-(thiophene-2-sulfonyl)-piperazine-2-carboxylic acid (1-oxo-2,3,4,9-tetrahydro-1H-beta-carbolin-6-yl)-amide 4-(thiophene-2-sulfonyl)-piperazine-1,3-dicarboxylic acid 3-[(9-ethyl-9H-carbazol-3-yl)-amide] 1-[(3-imidazol-1-yl-ethyl)-amide])

Chiral

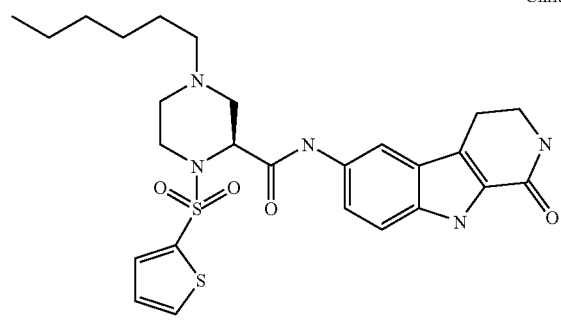

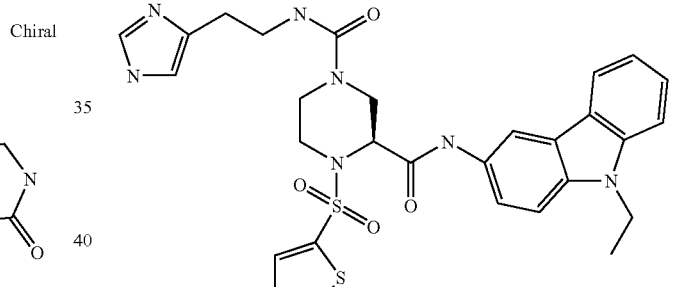

4-heptyl-1-(thiophene-2-sulfonyl)-piperazine-2-carboxylic acid (1-ethyl-2-pyridin-3-yl-1H-benzoimidazol-5-yl)-amide 4-pentyl-1-(thiophene-2-sulfonyl)-piperazine-2-carboxylic acid (1-oxo-2,3,4,9-tetrahydro-1H-beta-carbolin-6-yl)amide

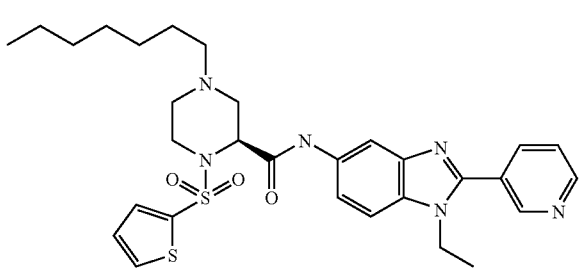

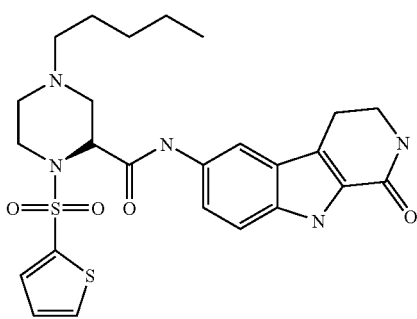

17

4-heptyl-1-(thiophene-2-sulfonyl)-piperazine-2-carboxylic acid (1-oxo-2,3,4,9-tetrahydro-1H-beta-carbolin-6-yl)amide

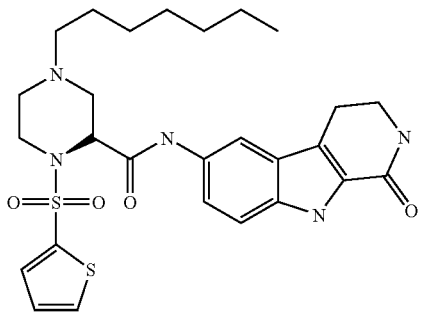

4-(3-methylsulfanyl-propyl)-1-(thiophene-2-sulfonyl)-piperazine-2-carboxylic acid (9-ethyl-9H-carbazol-3-yl)-amide

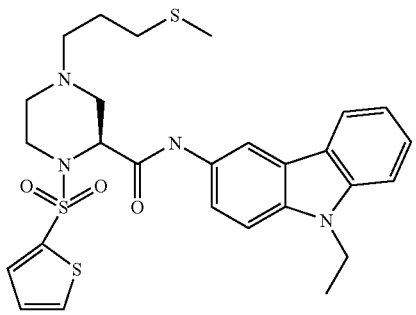

4-(4-ethyl-furan-3-ylmethyl)-1-(thiophene-2-sulfonyl)-piperazine-2-carboxylic acid (9-ethyl-9H-carbazol-3-yl)-amide

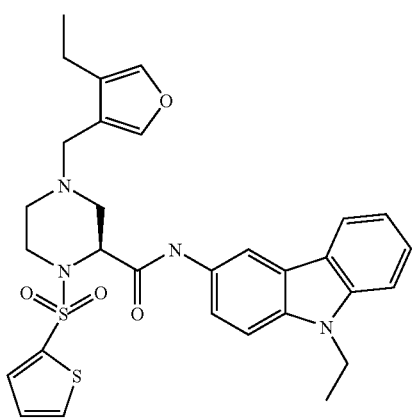

18

3-(9-ethyl-9H-carbazol-3-yl)-4-(thiophene-2-sulfonyl)-piperazin-1-yl]acetic acid ethyl ester

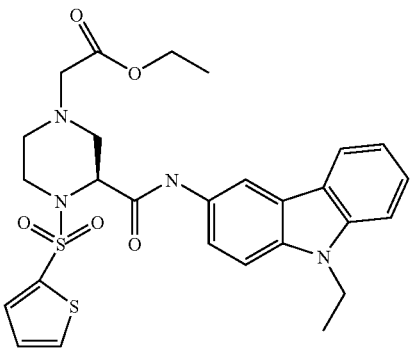

1-benzenesulfonyl-4-hexyl-piperazine-2-carboxylic acid (1-ethyl-2-pyridin-3-yl-1H-benzoimidazol-5-yl)amide

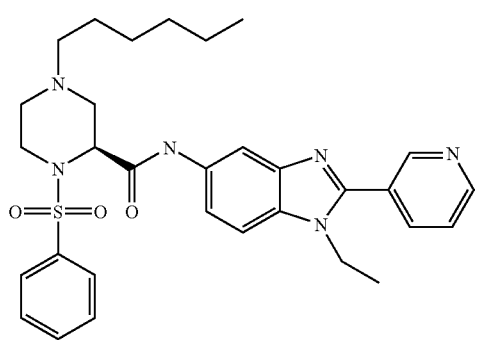

4-pentyl-1-thiophene-2-sulfonyl)-piperazine-2-carboxylic acid (1-ethyl-2-pyridin-3-yl-1H-benzoimidazol-5-yl)amide

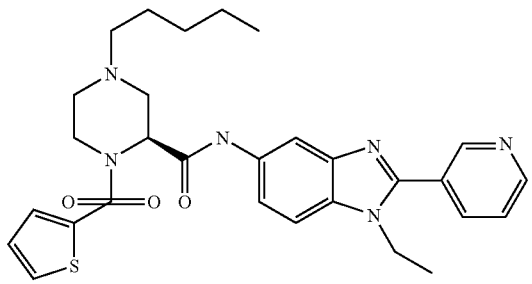

4-hexyl-1-thiophene-2-sulfonyl)-piperazine-2-carboxylic acid (1-ethyl-2-pyridin-3-yl-1H-benzoimidazol-5-yl)amide Chiral

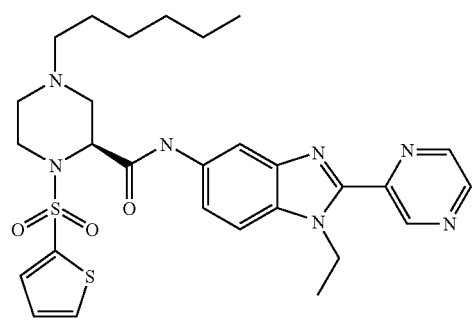

1-(4-fluoro-benzenesulfonyl)-4-hexyl-piperazine-2-carboxylic acid (1-ethyl-2-pyridin-3-yl-1H-benzoimidazol-5-yl)amide

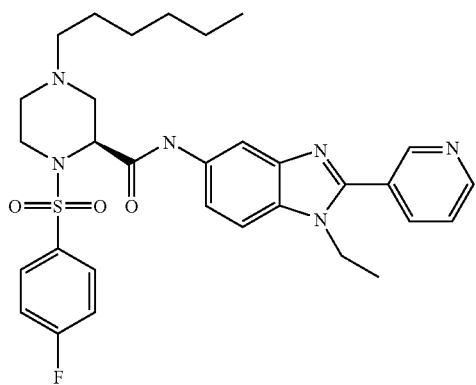

1-(2-fluoro-benzenesulfonyl)-4-hexyl-piperazine-2-carboxylic acid (1-ethyl-2-pyridin-3-yl-1H-benzoimidazol-5-yl)amide

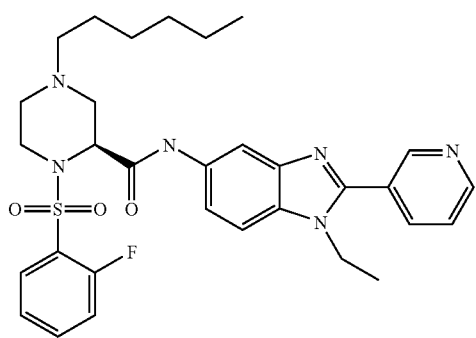

4-octyl-1-(thiophene-2-sulfonyl)-piperazine-2-carboxylic acid (1-ethyl-2-pyridin-4-yl-1H-benzoimidazol-5-yl)amide

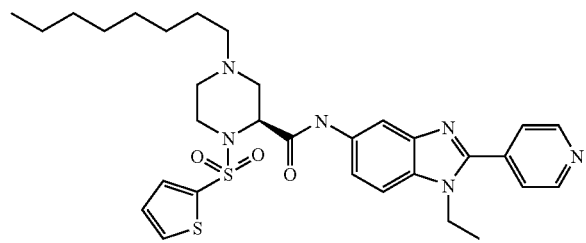

4-heptyl-1-(thiophene-2-sulfonyl)-piperazine-2-carboxylic acid (1-ethyl-2-pyridin-4-yl-1H-benzoimidazol-5-yl)amide

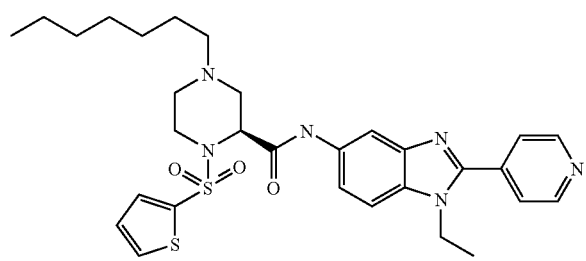

1-(butane-1-sulfonyl)-4-hexyl-piperazine-2-carboxylic acid (1-ethyl-2-pyridin-3-yl-1H-benzoimidazol-5-yl)amide

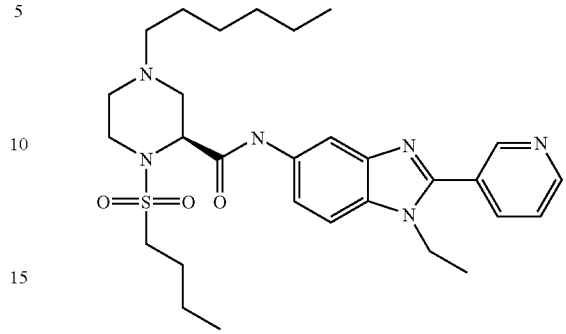

4-hexyl-1-(thiophene-2-sulfonyl)-piperazine-2-carboxylic acid (1-ethyl-2-pyridin-4-yl-1H-benzoimidazol-5-yl)amide 4-(3-methylsulfanyl-propyl)-1-(thiophene-2-sulfonyl)-piperazine-2-carboxylic acid (1-ethyl-2-pyridin-4-yl-1H-benzoimidazol-5-yl)amide

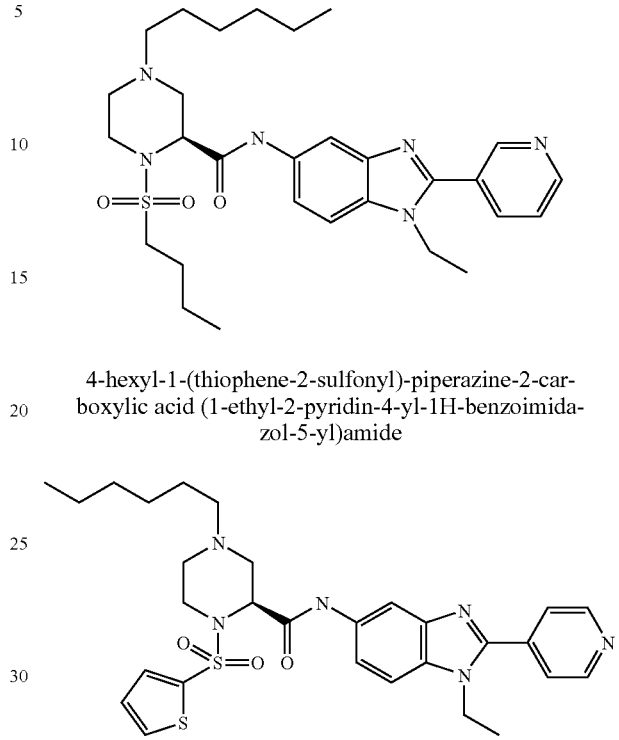

4-octyl-1-(thiophene-2-sulfonyl)-piperazine-2-carboxylic acid (1-ethyl-2-pyridin-3-yl-1H-benzoimidazol-5-yl)amide

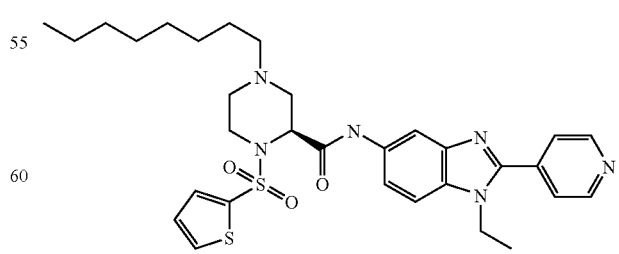

Compounds of the invention can be readily prepared. For instance, a suitable reaction sequence to provide compounds of the invention is set forth in the following Schemes 1A and 1B:

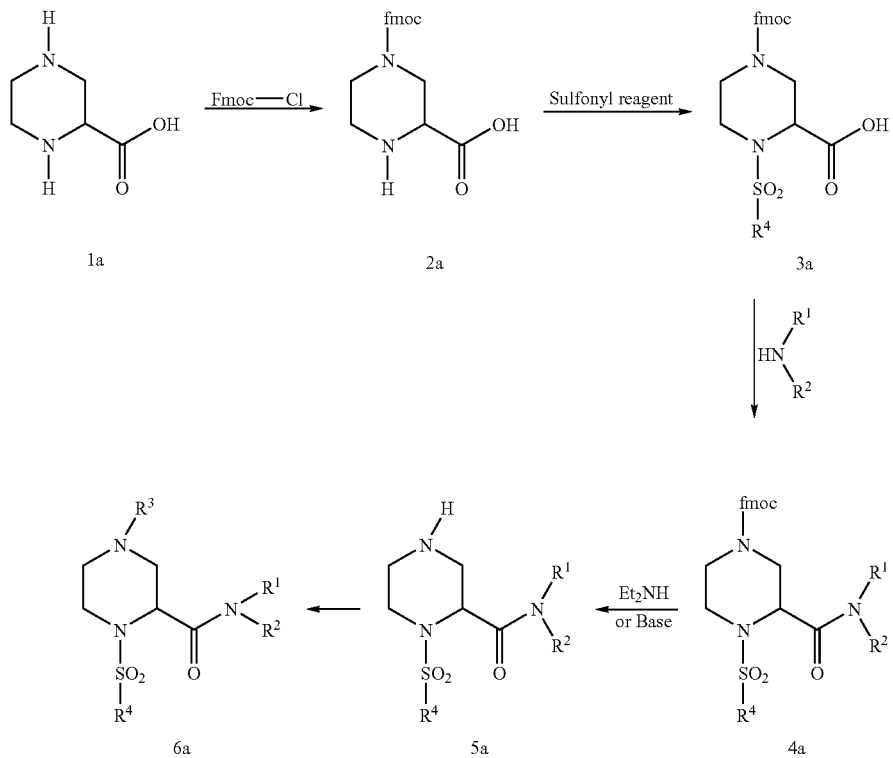

As exemplified in the above Scheme 1A of the ring nitrogens of a 2-carboxylic acid piperazine 1a (1) can be protected e.g. with FMOC chloride (9-fluorenylmethoxycarbonyl chloride) to lead a compound 2a (2). The unprotected ring nitrogen of compound 2a can be reacted with a sulfonyl reagent to introduce the —$SO_2R^4$ substituent of Formulae I to III, leading to sulfonyl derivatives of formula 3a such as for example an optionally substituted thiophene sulfonyl compound 3 as shown in Scheme 1B below.

The 2-carboxy group then can be functionalized to provide the carboxamide moiety, suitably by reaction with a primary or secondary amine of formula $HNR^1R^2$, where the amine reagent substituents provide $R^1$ and $R^2$ groups as defined in Formulae I to III above, such as to provide amide derivative of formula 4a, such as for example compound 4 as shown in Scheme 1B below.

The protected ring nitrogen then can be deprotected e.g. in the presence of base such as diethyl amine or other organic base, to provide a compound of formula 5a, for example a compound 5 of Scheme 1B below. The deprotected ring nitrogen then may be substituted as desired to provide an $R^3$ substituent, as defined in Formulae I to III above to lead to a compound of formula 6a, e.g. reacted with an optionally substituted alkyl chloride, optionally substituted benzyl chloride and the like to provide the corresponding $R^3$ moiety, such as compound 6 in the Scheme 1B below.

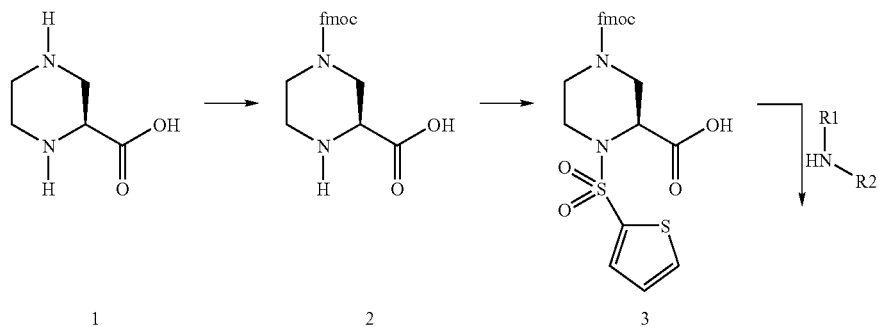

-continued

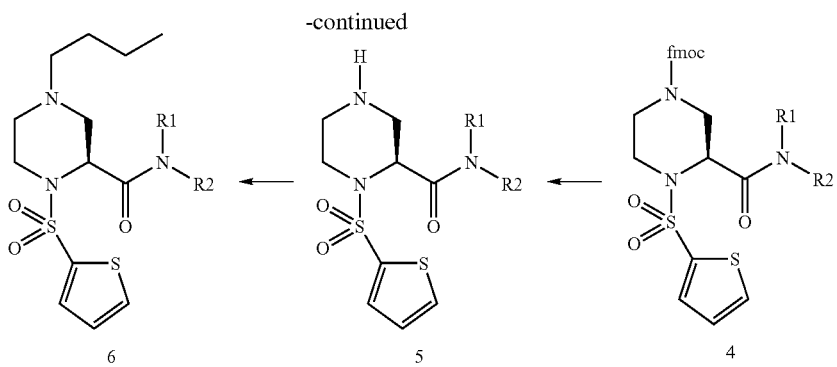

If the above set out general synthetic methods are not applicable for obtaining certain compounds of formula I, suitable methods of preparation known by a person skilled in the art should be used.

A particularly preferred reaction route to provide compounds of the invention is set forth in Example 1, which follows.

As discussed above, the present invention includes methods for treating infertility in male and female mammals, such as primates, particularly humans. Compounds of the invention will be useful for treatment of infertility conditions currently treated with FSH and/or LH, including female infertility and male spermatogenesis disorders.

The therapeutic methods of the invention generally comprise administration of an effective amount of one or more compounds of the invention to a subject including a mammal, such as a primate, especially a human, in need of such treatment.

Typical candidates for treatment in accordance with the methods of the invention persons suffering from or suspected of suffering from infertility. See the Merck Maitual, vol. 2, pages 12-17 (16th ed.) for identification of patients suffering from or suspected of infertility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g. to simulate follicular development and maturation. Compounds of the invention also can be administered to males to facilitate adequate spermatogenesis.

The treatment methods of the invention also will be useful for treatment of infertility in mammals other than humans, such as horses and livestock e.g. cattle, sheep, cows and the like.

Compounds of the invention may be administered as a "cocktail" formulation, i.e. coordinated administration of one or more compounds of the invention together with one or more other active therapeutics, particularly one or more other known fertility agents. For instance, one or more compounds of the invention may be administered in coordination with a regime of Follicle Stimulating Hormone and/or Leutinizing Hormone such as Gonal-F, Metrodin HP or Pergonal, or other agent such as clomephine citrate.

The compounds of this invention can be administered by a variety of routes, such as orally or by injection, e.g., intramuscular, intraperitoneal, subcutaneous or intravenous injection, or topically e.g. transdermally, vaginally and the like. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For oral administration, pharmaceutical compositions containing one or more substituted piperazine compounds of the invention may be formulated as e.g. tablets, troches, lozenges, aqueous or oil suspensions, dispersible powders or granules, emulsions, hard or soft capsules, syrups, elixers and the like. Typically, suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oil or aqueous solutions, as well as suspensions, emulsions, or implants, including suppositories. Ampules are convenient unit dosages.

For topical applications, formulations may be prepared in a topical ointment or cream containing one or more compounds of the invention. When formulated as an ointment, one or more compounds of the invention suitably may be employed with either a paraffinic or a water-miscible base. The one or more compounds also may be formulated with an oil-in-water cream base. Other suitable topical formulations include e.g. lozenges and dermal patches.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also Remington's Pharmaceutical Sciences. In general, a suitable effective dose of one or more compounds of the invention, particularly when using the more potent compound (s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals throughout the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein.

The following non-limiting examples are illustrative of the invention.

The following abbreviations refer respectively to the definitions below:

h (hour), g (gram), mg (milligram), min (minute), mM (millimolar), mL (milliliter). cAmP (Cyclic Adenosine Monophosphate); CHO (Chinese Hamster Ovary); DMF (dimethylformamide); DMSO (Dimethyl Sulfoxide); FSH (Follicle Stimulating Hormone); Fmoc (9-fluorenylmethoxycarbonyl); Gs (G-proteins); HATU (0-(7-azabenzotriazol-1-yl)-1, 1,3,3-tetramethyluronium hexafluorophosphate); HTS (High-Troughput Screening); LDR (Log-Dose Response); PDE (Phosphodiesterase); RT (Room Temperature); TSH (Tyroid Stimulating Hormone).

Example 1

Synthesis of 4-Hexyl-1-(thiophene-2-sulfonyl)-piperazine-2-carboxylic acid (1-ethyl-2-pyridin-3-yl-1H-benzoimidazol-5-yl)-amide The title compound was prepared as outlined in the following Scheme 2.

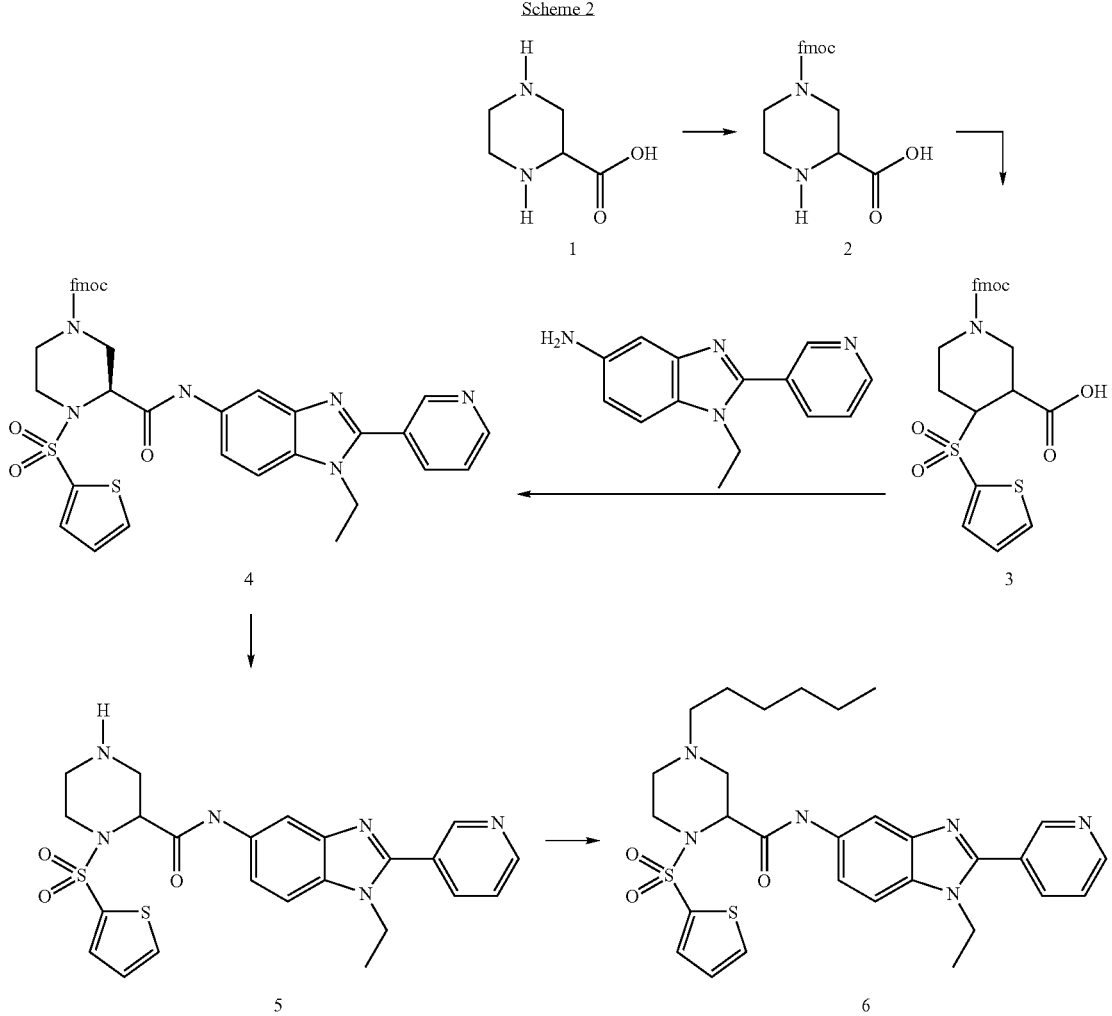

Part 1: Synthesis of Piperazine-1,3(R)-dicarboxylic acid-1-(9H-fluoren-9-ylmethyl)ester (Compound 2 in above Scheme 2)

Piperazine-2(R)-carboxylic acid dihydrochloride (5.95 g) was added to 50 mL dioxane/water (1:1). The solution was cooled in an ice bath and aqueous sodium hydroxide (10% w/v) solution was added drop-wise to adjust the pH to 9~10. At this pH, piperazine-2-carboxylic acid dissolved completely. Then, Fmoc Chloride (2.46 g) in dioxane was added drop-wise to the ice-cooled solution of piperazine and the reaction mixture was stirred from 0° C. to RT over 5-6 hr. The mixture was poured into 800 ml of ice water and washed once with ether. Then the aqueous phase was acidified to pH 2-3 with 2N of HCl which precipitated a white solid. This solid was filtered and dried in vacuo to obtain 2.46 g of a white powder. MS (ESI pos.): 353 (M+H).

Part 2: Synthesis of 4-(Thiophene-2-sulfonyl)-piperazine-1,3(R)-dicarboxylic acid 1-(9H-fluoren-9-ylmethyl)ester (Compound 3 in above Scheme 2).

4-Fmoc protected piperazine-2(R)-carboxylic acid (352 mg) was dissolved in 10 mL anhydrous methylene chloride. The solution was cooled in an ice bath and 0.35 mL di-isopropyl ethyl amine was added. Then, 183 mg of 2-thiophene sulfonyl chloride was added and the reaction mixture was stirred at 0° C. for 5 hr. The mixture was diluted with dichloromethane, washed with 0.5N aqueous hydrochloric acid and brine. The solvent was evaporated from the organic layer to leave a yellowish solid which was dried in vacuo. This crude material was used as such for the next step without purification.

Part 3: Synthesis of 3-(1-Ethyl-2-pyridin-3-yl-1H-benzoimidazol-5-ylcarbamoyl)-4-(thiophene-2-sulfonyl)-piperazine-1-carboxylic acid 9H-fluoren-9-ylmethyl ester (Compound 4 in above Scheme 2)

The crude material from the previous step was dissolved in anhydrous DMF and to this were added 238 mg of 1-Ethyl-2-pyridin-3-yl-1H-benzoimidazol-5-ylamine followed by 258 mg of di-isopropyl ethyl amine and 380 mg of HATU. The mixture was stirred for 5 hr upon which the crude mixture was diluted with ethyl acetate and the organic layer was successively washed with saturated sodium bicarbonate, 0.5N HCl and brine. The organic layer was evaporated to dryness and the product was isolated by chromatography over silica gel (0 to 5% methanol in ethyl acetate). MS (ESI pos.): 719 (M+H).

Part 4: Deprotection of Fmoc (9H-fluoren-9-ylmethyl ester) group

The Fmoc-protected piperazine derivative from step 3 was dissolved in 5 mL dichloromethane. To this were slowly added 5 mL of diethyl amine and the resulting mixture was stirred for 1.5 hr at ambient temperature. The excess reagent was evaporated in vacuo and the crude product was purified by chromatography over silica gel (0-25% methanol in ethyl acetate) to afford the piperazine 5. MS (ESI pos.): 497 (M+H)

Part 5: Synthesis of 4Hexyl-1-(thiophene-2-sulfonyl)-piperazine-2-carboxylic acid (1-ethyl-2-pyridin-3-yl-1H-benzoimidazol-5-yl)-amide (Compound 6 in above Scheme 2)

The piperazine 5 (200 mg) as prepared in Part 4 above was dissolved in dichloromethane containing 5% acetic acid and 144 microliters of n-hexanal were added. After stirring for 16 hours, 500 mg of sodium cyano borohydride was added and the reaction was stirred for 5 hr at room temperature. The crude mixture was washed with saturated sodium bicarbonate, brine and dried. Purification over silica gel (0-5% methanol in ethyl acetate) afforded 126 mg of the desired product 6. MS (ESI pos.): 581 (M+H)

Example 2

FSH Assay Method

Compounds of the invention were tested in the following assay.

Assay Overview.

All compounds of the invention were stored in 96-well deepwell plates in DMSO at a nominal concentration of 10 μM. Compounds of the invention were screened for agonist activity at the FSH receptor using the recombinant FSH receptor stably transfected and expressed in Chinese Hamster Ovary Cells (CHO cells) essentially as described in the work by Kelton, et al. Molecular and Cellular Endocrinology, 1992, 89, 141-151). Since the FSH receptor is known to act via a G-protein (Gs) to activate adenylyl cyclase and hence raise intracellular levels of cAMP the high throughput screening (HTS) assay used a gene reporter system consisting of the cAMP response element coupled upstream to the reporter gene which, in this case was the enzyme luciferase. Thus an agonist at the FSH receptor increases cAMP in the cell which results in activation of the CREB (cAMP) response element binding protein). The substrate for the enzyme (Packard Instrument Company 800 Research Parkway, Meriden, Conn. 06450, USA) was added to the cells after appropriate incubation with the compounds or FSH and the amount of luciferase expressed was measured by quantitating the luminescence produced by the enzyme using a TopCount scintillation/luminescence counter running in single photon counting mode. A compound which acts as an agonist at the receptor should produce light from the treated cells in proportion to its concentration within the incubation. Luminescence should be saturable at high concentrations of the compound.

Protocol.

The compounds of the invention, in deepwell plates (Master plates) as indicated above were loaded on the robotic deck along with the appropriate number of assay plates and daughter plates. A 10 μl aliquot from each master plate was transferred to the corresponding daughter plate and 90 μl of DME/F12 was added and mixed within each well. 20 μl was then removed from the daughter plate and dispensed into the assay plate. After addition of an aliquot of FSH (equivalent to an EC100 response for this hormone to each of three wells on the plate, 80 μl of media (DME/F 12±2% serum) and 100 μl aliquot of cells ($4 \times 10^5$/ml in the same media) were added and the plate incubated at 37° C. for 3 hrs 30 min. At this time the plate was removed from the incubator and media in each well was aspirated and the cells adhering to the bottom of the plate washed with 300 μl PBS containing 1 mM $Ca^{2+}$ and 1 mM $Mg^{2+}$. The PBS was aspirated and 100 μl PBS added to each well. 100 μl of Lucite (prepared as described by the manufacturer) was added to each well and the plate was shaken gently for 40 seconds prior to placement in the TopCount plate reader. After allowing 3.5 minutes for the plate to dark-adapt within the machine, the amount of luminescence generated was quantitated using Single Photon Counting mode. The data was transmitted electronically from the TopCount to the robot processing computer terminal and was renamed with an ID corresponding to the original master plate ID. Data was evaluated using an Excel macro and compounds showing activity comparable to that produced by an ED100 of FSH itself were further analyzed in the same assay at differing concentrations. LDR (log-dose-response) curves were generated for these compounds in CHO cells containing the FSH receptor and these curves were also compared with those in either cells expressing a different Gs linked receptor or in cells lacking any transfected receptor. Results are set forth in the following Table 1.

TABLE 1

| Tested Compound | $ED_{50}$ (nM) |
|---|---|
| 4-hexyl-1-(thiophene-2-sulfonyl)-piperazine-2-carboxylic acid (1-ethyl-2-pyridinyl-3-yl-1H-benzoimidazol-5-yl)-amide) | 40 |
| 4-(thiophene-2-sulfonyl)-piperazine-1,3-dicarboxylic acid 3-[(9-ethyl-9H-carbazol-3-yl)amide]-1-pentylamide | 63 |
| 4-(thiophene-2-sulfonyl)-piperazine-1,3-dicarboxylic acid 1-ethylamide 3-[(9-ethyl-9H-carbazol-3-yl)amide] | 877 |
| {[3-(9-ethyl-9H-carbazol-3-ylcarbamoyl)-4-(thiophene-2-sulfonyl)-piperazine-1-carbonyl]-amino} acetic acid ethyl ester | 408 |
| 4-pentanoyl-1-(thiophene-2-sulfonyl)-piperazine-2-carboxylic acid (9-ethyl-9H-carbazol-3-yl) amide | 402 |
| 4-hexyl-1-(thiophene-2-sulfonyl)-piperazine-2-carboxylic acid (9-ethyl-9H-carbazol-3-yl) amide | 380 |
| 4-dimethylsulfamoyl-piperazine-1,3-dicarboxylic acid 3-[(9-ethyl-9H-carbazol-3-yl)amide] 1-pentylamide | 403 |
| 4-(1-methyl-1H-imidazole-4-sulfonyl)-piperazine-1,3-dicarboxylic acid 3-[(9-ethyl-9H-carbazol-3-yl)-amide] 1-pentylamide | 3160 |
| 4-(thiophene-2-sulfonyl)-piperazine-1,3-dicarboxyclic acid 1-pentylamide 3-[(3-pyridin-4-yl-phenyl)-amide] | 5000 |
| 4-(thiophene-2-sulfonyl)-piperazine-1,3-dicarboxylic acid 3-[(9-ethyl-9H-carbazol-3-yl)-amide] 1-{[2-(1H-imidazol-4-yl)-ethyl]-amide} | 6250 |
| 4-hexyl-1-(thiophene-2-sulfonyl)-piperazine-2-carboxylic acid (1-oxo-2,3,4,9-tetrahydro-1H-beta-carbolin-6-yl)-amide | 978 |
| 4-heptyl-1-(thiophene-2-sulfonyl)-piperazine-2-carboxylic acid (1-ethyl-2-pyridin-3-yl-1H-benzoimidazol-5-yl)-amide | 94 |
| 4-(thiophene-2-sulfonyl)-piperazine-1,3-dicarboxylic acid 3-[(9-ethyl-9H-carbazol-3-yl)-amide] 1-[(3-imidazol-1-yl propyl)-amide]) | 6470 |
| 4-pentyl-1-(thiophene-2-sulfonyl)-piperazine-2-carboxylic acid (1-oxo-2,3,4,9-tetrahydro-1H-beta-carbolin-6-yl)amide | 220 |
| 4-heptyl-1-(thiophene-2-sulfonyl)-piperazine-2-carboxylic acid (1-oxo-2,3,4,9-tetrahydro-1H-beta-carbolin-6-yl)amide | 1200 |
| 4-(3-methylsulfanyl-propyl)-1-(thiophene-2-sulfonyl)-piperazine-2-carboxylic acid (9-ethyl-9H-carbazol-3-yl)-amide | 1700 |
| 4-(4-ethyl-furan-3-ylmethyl)-1-(thiophene-2-sulfonyl)-piperazine-2-carboxylic acid (9-ethyl-9H-carbazol-3-yl)-amide | 1600 |
| 3-(9-ethyl-9H-carbazol-3-ylcarbamoyl)-4-(thiophene-2-sulfonyl)-piperazin-1-yl] acetic acid ethyl ester | 610 |
| 1-benzenesulfonyl-4-hexyl-piperazine-2-carboxylic acid (1-ethyl-2-pyridin-3-yl-1H-benzoimidazol-5-yl) amide | 150 |
| 4-pentyl-1-thiophene-2-sulfonyl)-piperazine-2-carboxylic acid (1-ethyl-2-pyridin-3-yl-1H-benzoimidazol-5-yl) amide | 150 |
| 4-hexyl-1-thiophene-2-sulfonyl)-piperazine-2-carboxylic acid (1-ethyl-2-pyridin-3-yl-1H-benzoimidazol-5-yl) amide | 180 |
| 1-(4-fluoro-benzenesulfonyl)-4-hexyl-piperazine-2-carboxylic acid (1-ethyl-2-pyridin-3-yl-1H-benzoimidazol-5-yl) amide | 167 |
| 1-(2-fluoro-benzenesulfonyl)-4-hexyl-piperazine-2-carboxylic acid (1-ethyl-2-pyridin-3-yl-1H-benzoimidazol-5-yl) amide | 74 |
| 4-octyl-1-(thiophene-2-sulfonyl)-piperazine-2-carboxylic acid (1-ethyl-2-pyridin-4-yl-1H-benzoimidazol-5-yl) amide | 54 |
| 4-heptyl-1-(thiophene-2-sulfonyl)-piperazine-2-carboxylic acid (1-ethyl-2-pyridin-4-yl-1H-benzoimidazol-5-yl) amide | 53 |
| 1-dimethylsulfamoyl-4-hexyl-piperazine-2-carboxylic acid (1-ethyl-2-pyridin-3-yl-1H-benzoimidazol-5-yl) amide | 242 |
| 1-(butane-1-sulfonyl)-4-hexyl-piperazine-2-carboxylic acid (1-ethyl-2-pyridin-3-yl-1H-benzoimidazol-5-yl) amide | 170 |
| 4-hexyl-1-(thiophene-2-sulfonyl)-piperazine-2-carboxylic acid (1-ethyl-2-pyridin-4-yl-1H-benzoimidazol-5-yl) amide | 111 |

TABLE 1-continued

| Tested Compound | $ED_{50}$ (nM) |
|---|---|
| 4-(3-methylsulfanyl-propyl)-1-(thiophene-2-sulfonyl)-piperazine-2-carboxylic acid (1-ethyl-2-pyridin-4-yl-1H-benzoimidazol-5-yl) amide | 14000 |
| 4-(thiophene-2-sulfonyl)-piperazine-1,3-dicarboxylic acid 3-[(9-ethyl-9H-carbazol-3-yl)-amide] 1-[(2-methoxy-ethyl)-amide] | 1610 |
| 4-octyl-1-(thiophene-2-sulfonyl)-piperazine-2-carboxylic acid (1-ethyl-2-pyridin-3-yl-1H-benzoimidazol-5-yl) amide | 13 |

The invention has been described in detail with reference to preferred embodiments thereof. However, it will be appreciated that those skilled in the art, upon consideration of this disclosure, may make modifications and improvements within the spirit and scope of the invention.

What is claimed is:

1. A compound according to Formula I:

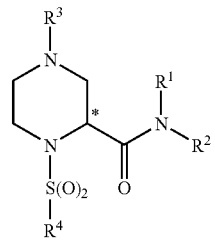

I wherein $R^1$ is H;
$R^2$ is selected from aryl, heteroaryl, 3-8-membered cycloalkyl and heterocycloalkyl;
$R^3$ is selected from $C_1$-$C_{16}$-alkyl, $C_2$-$C_{16}$-alkenyl, $C_2$-$C_{16}$-alkynyl, monocyclic aryl, monocyclic heteroaryl, 3-8-membered monocyclic cycloalkyl, monocyclic heterocycloalkyl, acyl, $C_1$-$C_{16}$-alkyl aryl, $C_1$-$C_{16}$-alkyl heteroaryl, $C_2$-$C_{16}$-alkenyl aryl, $C_2$-$C_{16}$-alkenyl heteroaryl, $C_2$-$C_{16}$-alkynyl aryl, $C_2$-$C_{16}$-alkynyl heteroaryl, $C_1$-$C_{16}$-alkyl cycloalkyl, $C_1$-$C_{16}$-alkyl heterocycloalkyl, $C_2$-$C_{16}$-alkenyl cycloalkyl, $C_2$-$C_{16}$-alkenyl heterocycloalkyl, $C_2$-$C_{16}$-alkynyl cycloalkyl, $C_2$-$C_{16}$-alkynyl heterocycloalkyl, alkoxycarbonyl, aminocarbonyl, $C_1$-$C_{16}$-alkyl carboxy, $C_1$-$C_{16}$-alkyl acyl, aryl acyl, heteroaryl acyl, $C_3$-$C_8$-(hetero)cycloalkyl acyl, $C_1$-$C_{16}$-alkyl acyloxy, $C_1$-$C_{16}$-alkyl alkoxy, $C_1$-$C_{16}$-alkyl alkoxycarbonyl, aminocarbonyl, $C_1$-$C_{16}$-alkyl acylamino, acylamino, $C_1$-$C_{16}$-alkyl sulfinyl, $C_1$-$C_{16}$-alkyl sulfanyl, $C_1$-$C_{16}$-alkyl ureido, $C_1$-$C_{16}$-alkyl carbamate, $C_1$-$C_{16}$-alkyl amino, $C_1$-$C_{16}$-alkyl ammonium;
$R^4$ is selected from $C_1$-$C_{12}$-alkyl, $C_2$-$C_{12}$-alkenyl, $C_2$-$C_{12}$-alkynyl, aryl, heteroaryl, 3-8-membered cycloalkyl, heterocycloalkyl, and amino; and pharmaceutically acceptable salts thereof.

2. The compound of claim 1 wherein $R^2$ is aryl or heteroaryl.

3. The compound of claim 1, wherein $R^4$ is selected from $C_1$-alkyl, amino, aryl, heteroaryl, 3-8-membered cycloalkyl and heterocycloalkyl.

4. The compound of claim 1, wherein $R^2$ is aryl; $R^3$ is selected from $C_1$-$C_8$-alkyl, $C_1$-$C_8$-acyl amino and $C_1$-$C_8$-alkyl acyl and $R^4$ is selected from $C_1$-$C_6$-alkyl, amino, aryl and heteroaryl.

5. The compound of claim 1, wherein $R^2$ is fused phenyl.

6. The compound of claim 1, wherein $R^4$ is thienyl.

7. The compound of claim 1 having the following Formula II:

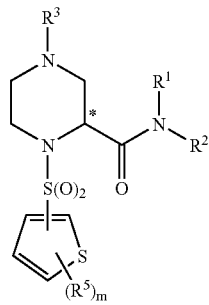

wherein
$R^5$ is independently halogen or hydroxy; m is an integer of from 0 to 3; and pharmaceutically acceptable salts thereof.

8. The compound of claim 1 wherein $R^2$ comprises a carbazolyl, tetrahydro-beta-carbolinyl or a benzimidazolyl moiety.

9. The compound of claim 1 that is selected from the following group:
 4-hexyl-1-(thiophene-2-sulfonyl)-piperazine-2-carboxylic acid (1-ethyl-2-pyridinyl-3-yl-1H-benzoimidazol-5-yl)-amide);
 4-(thiophene-2-sulfonyl)-piperazine-1,3-dicarboxylic acid 3-[(9-ethyl-9H-carbazol-3-yl)amide]-1-pentylamide;
 4-(thiophene-2-sulfonyl)-piperazine-1,3-dicarboxylic acid 1-ethylamide 3-[(9-ethyl-9H-carbazol-3-yl)amide];
 4-pentanoyl-1-(thiophene-2-sulfonyl)-piperazine-2-carboxylic acid (9-ethyl-9H-carbazol-3-yl)amide;
 4-hexyl-1-(thiophene-2-sulfonyl)-piperazine-2-carboxylic acid (9-ethyl-9H-carbazol-3-yl)amide;
 4-dimethylsulfamoyl-piperazine-1,3-dicarboxylic acid 3-[(9-ethyl-9H-carbazol-3-yl)amide] 1-pentylamide;
 4-(1-methyl-1H-imidazole-4-sulfonyl)-piperazine-1,3-dicarboxylic acid 3-[(9-ethyl-9H-carbazol-3-yl)-amide] 1-pentylamide;
 4-(thiophene-2-sulfonyl)-piperazine-1,3-dicarboxyclic acid 1-pentylamide 3-[(3-pyridin-4-yl-phenyl)-amide];
 4-hexyl-1-(thiophene-2-sulfonyl)-piperazine-2-carboxylic acid (1-oxo-2,3,4,9-tetrahydro-1H-beta-carbolin-6-yl)-amide;
 4-heptyl-1-(thiophene-2-sulfonyl)-piperazine-2-carboxylic acid (1-ethyl-2-pyridin-3-yl-1H-benzoimidazol-5-yl)-amide;
 4-pentyl-1-(thiophene-2-sulfonyl)-piperazine-2-carboxylic acid (1-oxo-2,3,4,9-tetrahydro-1H-beta-carbolin-6-yl)amide;
 4-heptyl-1-(thiophene-2-sulfonyl)-piperazine-2-carboxylic acid (1-oxo-2,3,4,9-tetrahydro-1H-beta-carbolin-6-yl)amide;
 4-(3-methylsulfanyl-propyl)-1-(thiophene-2-sulfonyl)-piperazine-2-carboxylic acid (9-ethyl-9H-carbazol-3-yl)-amide;
 4-(4-ethyl-furan-3-ylmethyl)-1-(thiophene-2-sulfonyl)-piperazine-2-carboxylic acid (9-ethyl-9H-carbazol-3-yl)-amide;
 3-(9-ethyl-9H-carbazol-3-ylcarbamoyl)-4-(thiophene-2-sulfonyl)-piperazin-1-yl]acetic acid ethyl ester;
 1-benzenesulfonyl-4-hexyl-piperazine-2-carboxylic acid (1-ethyl-2-pyridin-3-yl-1H-benzoimidazol-5-yl)amide;
 4-pentyl-1-thiophene-2-sulfonyl)-piperazine-2-carboxylic acid (1-ethyl-2-pyridin-3-yl-1H-benzoimidazol-5-yl)amide;
 4-hexyl-1-thiophene-2-sulfonyl)-piperazine-2-carboxylic acid (1-ethyl-2-pyridin-3-yl-1H-benzoimidazol-5-yl)amide;
 1-(4-fluoro-benzenesulfonyl)-4-hexyl-piperazine-2-carboxylic acid (1-ethyl-2-pyridin-3-yl-1H-benzoimidazol-5-yl)amide;
 1-(2-fluoro-benzenesulfonyl)-4-hexyl-piperazine-2-carboxylic acid (1-ethyl-2-pyridin-3-yl-1H-benzoimidazol-5-yl)amide;
 4-octyl-1-(thiophene-2-sulfonyl)-piperazine-2-carboxylic acid (1-ethyl-2-pyridin-4-yl-1H-benzoimidazol-5-yl)amide;
 4-heptyl-1-(thiophene-2-sulfonyl)-piperazine-2-carboxylic acid (1-ethyl-2-pyridin-4-yl-1H-benzoimidazol-5-yl)amide;
 1-dimethylsulfamoyl-4-hexyl-piperazine-2-carboxylic acid (1-ethyl-2-pyridin-3-yl-1H-benzoimidazol-5-yl)amide;
 1-(butane-1-sulfonyl)-4-hexyl-piperazine-2-carboxylic acid (1-ethyl-2-pyridin-3-yl-1H-benzoimidazol-5-yl)amide;
 4-hexyl-1-(thiophene-2-sulfonyl)-piperazine-2-carboxylic acid (1-ethyl-2-pyridin-4-yl-1H-benzoimidazol-5-yl)amide;
 4-(3-methylsulfanyl-propyl)-1-(thiophene-2-sulfonyl)-piperazine-2-carboxylic acid (1-ethyl-2-pyridin-4-yl-1H-benzoimidazol-5-yl)amide;
 4-octyl-1-(thiophene-2-sulfonyl)-piperazine-2-carboxylic acid (1-ethyl-2-pyridin-3-yl-1H-benzoimidazol-5-yl) amide; and pharmaceutically acceptable salts thereof.

10. A pharmaceutical composition comprising the compound of claim 9.

11. A pharmaceutical composition comprising a pharmaceutically acceptable carrier and one or more compounds of claim 9.

12. A pharmaceutical composition of claim 11 wherein the compound is packaged together with instructions for use of the compound to treat infertility.

13. The compound of claim 7 wherein m is an integer of from 0 to 2.

14. A method for treating infertility in a mammal, comprising administering to a mammal suspected of infertility a therapeutically effective amount of a compound of claim 1.

15. The method of claim 14, wherein $R^2$ is aryl or heteroaryl.

16. The method of claim 14, wherein $R^4$ is selected from $C_1$-$C_6$-alkyl, amino, aryl, heteroaryl, 3-8-membered cycloalkyl and heterocycloalkyl.

17. The method of treatment of claim 14, wherein $R^2$ is aryl; $R^3$ is selected from $C_1$-$C_8$-alkyl, $C_1$-$C_8$-acyl amino and $C_1$-$C_8$-alkyl acyl and $R^4$ is selected from $C_1$-$C_6$-alkyl, amino, aryl and heteroaryl.

18. The method of claim 14 wherein the compound has the following Formula II:

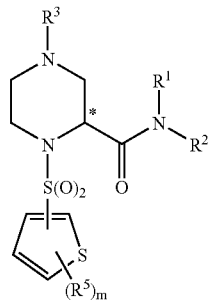

wherein $R^5$ is independently halogen or hydroxy;
m is an integer of from 0 to 3; and pharmaceutically acceptable salts thereof.

19. The method of claim 14 wherein $R^2$ comprises a carbazolyl, tetrahydro-beta-carbolinyl or benzimidazolyl moiety.

20. The method of claim 14 wherein the compound of formula I is selected from the following group:
   4-hexyl-1-(thiophene-2-sulfonyl)-piperazine-2-carboxylic acid (1-ethyl-2-pyridinyl-3-yl-1H-benzoimidazol-5-yl)-amide);
   4-(thiophene-2-sulfonyl)-piperazine-1,3-dicarboxylic acid 3-[(9-ethyl-9H-carbazol-3-yl)amide]-1-pentylamide;
   4-(thiophene-2-sulfonyl)-piperazine-1,3-dicarboxylic acid 1-ethylamide 3-[(9-ethyl-9H-carbazol-3-yl) amide];
   4-pentanoyl-1-(thiophene-2-sulfonyl)-piperazine-2-carboxylic acid (9-ethyl-9H-carbazol-3-yl)amide;
   4-hexyl-1-(thiophene-2-sulfonyl)-piperazine-2-carboxylic acid (9-ethyl-9H-carbazol-3-yl)amide;
   4-dimethylsulfamoyl-piperazine-1,3-dicarboxylic acid 3-[(9-ethyl-9H-carbazol-3-yl)amide] 1-pentylamide;
   4-(1-methyl-1H-imidazole-4-sulfonyl)-piperazine-1,3-dicarboxylic acid 3-[(9-ethyl-9H-carbazol-3-yl)-amide] 1-pentylamide;
   4-(thiophene-2-sulfonyl)-piperazine-1,3-dicarboxyclic acid 1-pentylamide 3-[(3-pyridin-4-yl-phenyl)-amide];
   4-hexyl-1-(thiophene-2-sulfonyl)-piperazine-2-carboxylic acid (1-oxo-2,3,4,9-tetrahydro-1H-beta-carbolin-6-yl)-amide;
   4-heptyl-1-(thiophene-2-sulfonyl)-piperazine-2-carboxylic acid (1-ethyl-2-pyridin-3-yl-1H-benzoimidazol-5-yl)-amide;
   4-pentyl-1-(thiophene-2-sulfonyl)-piperazine-2-carboxylic acid (1-oxo-2,3,4,9-tetrahydro-1H-beta-carbolin-6-yl)amide;
   4-heptyl-1-(thiophene-2-sulfonyl)-piperazine-2-carboxylic acid (1-oxo-2,3,4,9-tetrahydro-1H-beta-carbolin-6-yl)amide;
   4-(3-methylsulfanyl-propyl)-1-(thiophene-2-sulfonyl)-piperazine-2-carboxylic acid (9-ethyl-9H-carbazol-3-yl)-amide;
   4-(4-ethyl-furan-3-ylmethyl)-1-(thiophene-2-sulfonyl)-piperazine-2-carboxylic acid (9-ethyl-9H-carbazol-3-yl)-amide;
   3-(9-ethyl-9H-carbazol-3-ylcarbamoyl)-4-(thiophene-2-sulfonyl)-piperazin-1-yl]acetic acid ethyl ester;
   1-benzenesulfonyl-4-hexyl-piperazine-2-carboxylic acid (1-ethyl-2-pyridin-3-yl-1H-benzoimidazol-5-yl)amide;
   4-pentyl-1-thiophene-2-sulfonyl)-piperazine-2-carboxylic acid (1-ethyl-2-pyridin-3-yl-1H-benzoimidazol-5-yl)amide;
   4-hexyl-1-thiophene-2-sulfonyl)-piperazine-2-carboxylic acid (1-ethyl-2-pyridin-3-yl-1H-benzoimidazol-5-yl) amide;
   1-(4-fluoro-benzenesulfonyl)-4-hexyl-piperazine-2-carboxylic acid (1-ethyl-2-pyridin-3-yl-1H-benzoimidazol-5-yl)amide;
   1-(2-fluoro-benzenesulfonyl)-4-hexyl-piperazine-2-carboxylic acid (1-ethyl-2-pyridin-3-yl-1H-benzoimidazol-5-yl)amide;
   4-octyl-1-(thiophene-2-sulfonyl)-piperazine-2-carboxylic acid (1-ethyl-2-pyridin-4-yl-1H-benzoimidazol-5-yl) amide;
   4-heptyl-1-(thiophene-2-sulfonyl)-piperazine-2-carboxylic acid (1-ethyl-2-pyridin-4-yl-1H-benzoimidazol-5-yl)amide;
   1-dimethylsulfamoyl-4-hexyl-piperazine-2-carboxylic acid (1-ethyl-2-pyridin-3-yl-1H-benzoimidazol-5-yl) amide;
   1-(butane-1-sulfonyl)-4-hexyl-piperazine-2-carboxylic acid (1-ethyl-2-pyridin-3-yl-1H-benzoimidazol-5-yl) amide;
   4-hexyl-1-(thiophene-2-sulfonyl)-piperazine-2-carboxylic acid (1-ethyl-2-pyridin-4-yl-1H-benzoimidazol-5-yl)amide;
   4-(3-methylsulfanyl-propyl)-1-(thiophene-2-sulfonyl)-piperazine-2-carboxylic acid (1-ethyl-2-pyridin-4-yl-1H-benzoimidazol-5-yl)amide;
   4-octyl-1-(thiophene-2-sulfonyl)-piperazine-2-carboxylic acid (1-ethyl-2-pyridin-3-yl-1H-benzoimidazol-5-yl) amide; and pharmaceutically acceptable salts thereof.

21. The method of claim 14 wherein the mammal is a human.

22. The method of claim 21 wherein the mammal is a female.

23. The method of claim 22 wherein the mammal is suffering from an ovulatory disorder.

24. The method of claim 22 wherein the mammal is being treated with an assisted reproduction procedure.

25. The method of claim 22 wherein the mammal is undergoing in-vitro fertilization.

26. The method of claim 21 wherein the mammal is a male.

27. The method of claim 22 wherein the mammal is a male suffering from a spermatogenesis disorder.

* * * * *